US009744101B2

(12) United States Patent
Weibel

(10) Patent No.: US 9,744,101 B2
(45) Date of Patent: Aug. 29, 2017

(54) ADAPTER FOR A TRANSFER DEVICE FOR A FLUID, AND TRANSFER DEVICE

(75) Inventor: Ludwig Daniel Weibel, Waldstatt (CH)

(73) Assignee: Weibel CDS AG, Waldstatt (CH)

(*) Notice: Subject to any disclaimer, the term of this patent is extended or adjusted under 35 U.S.C. 154(b) by 678 days.

(21) Appl. No.: 14/239,295

(22) PCT Filed: Aug. 15, 2012

(86) PCT No.: PCT/EP2012/065955
§ 371 (c)(1),
(2), (4) Date: Jun. 5, 2014

(87) PCT Pub. No.: WO2013/024120
PCT Pub. Date: Feb. 21, 2013

(65) Prior Publication Data
US 2014/0305527 A1  Oct. 16, 2014

(30) Foreign Application Priority Data
Aug. 18, 2011  (EP) .................................... 11177918

(51) Int. Cl.
*A61J 1/20* (2006.01)
*A61M 39/10* (2006.01)

(52) U.S. Cl.
CPC ........... *A61J 1/2096* (2013.01); *A61J 1/2089* (2013.01); *A61M 39/10* (2013.01); *A61J 1/201* (2015.05);
(Continued)

(58) Field of Classification Search
CPC ......... A61J 1/201; A61J 1/2096; A61J 1/2065
(Continued)

(56) References Cited

U.S. PATENT DOCUMENTS 4,253,501 A    3/1981  Ogle
4,564,054 A *  1/1986  Gustavsson ........... A61J 1/2096
                                                   141/329
(Continued)

FOREIGN PATENT DOCUMENTS

FR    2509689    1/1983
FR    2753624    3/1998
WO    01/00261   1/2001

*Primary Examiner* — Timothy L Maust
*Assistant Examiner* — Timothy P Kelly
(74) *Attorney, Agent, or Firm* — Davis & Bujold PLLC; Michael J. Bujold

(57) ABSTRACT

The invention relates to an adapter (1) for a transfer device (20) for a fluid, for the connection of a container (17) containing the fluid, wherein the container (17) is closed by a pierceable closure element (18), and the adapter (1) has an attachment (4) which can be fitted sealingly, in an attachment direction, onto a container mouth closed by the closure element. A penetration element (6) is mounted on the attachment (4) in such a way that the penetration element (6) is movable, with the aid of guide means, between a rest position (R) and a withdrawal position (E), wherein the penetration element (6) has a hollow needle (9) with which the closure element (18) can be pierced in the withdrawal position (E). The adapter (1) has a connector stub (3) with a coupling for the fluid-tight connection of a further adapter (1'), and a transfer channel (10) runs from a mouth on the connector stub (3) to a mouth on the hollow needle (9), such that the mouth of the transfer channel (10) on the connector stub (3) communicates with an interior of the connected container (17) in the withdrawal position (E) of the penetration element (6). The invention is characterized in that the connector stub (3) is arranged transversely, in particular substantially perpendicularly, with respect to the attachment direction (H), preferably on the penetration element (6).

16 Claims, 11 Drawing Sheets

(52) U.S. Cl.
CPC ............ *A61J 1/2055* (2015.05); *A61J 1/2058* (2015.05); *A61J 1/2075* (2015.05); *A61J 1/2082* (2015.05); *Y10T 137/9029* (2015.04)

(58) Field of Classification Search
USPC ............ 141/329–330; 604/411, 412; 222/83
See application file for complete search history.

(56) References Cited

U.S. PATENT DOCUMENTS

| | | | | |
|---|---|---|---|---|
| 6,948,522 | B2* | 9/2005 | Newbrough | A61J 1/2089 137/550 |
| 8,596,310 | B2* | 12/2013 | Senno | B29C 73/166 141/105 |
| 2004/0225274 | A1* | 11/2004 | Jansen | A61J 1/2089 604/411 |
| 2009/0177178 | A1* | 7/2009 | Pedersen | A61J 1/2089 604/414 |

* cited by examiner

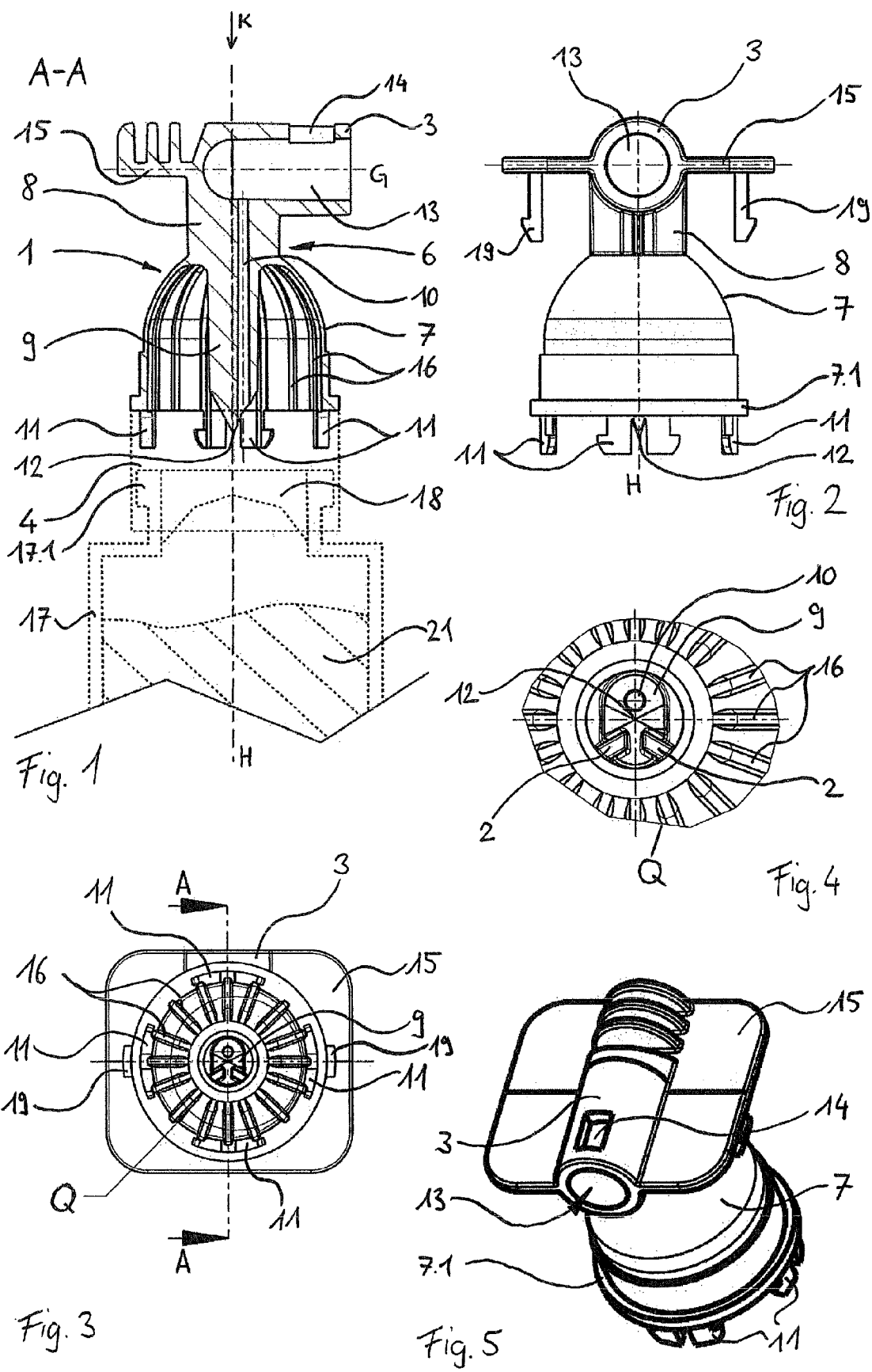

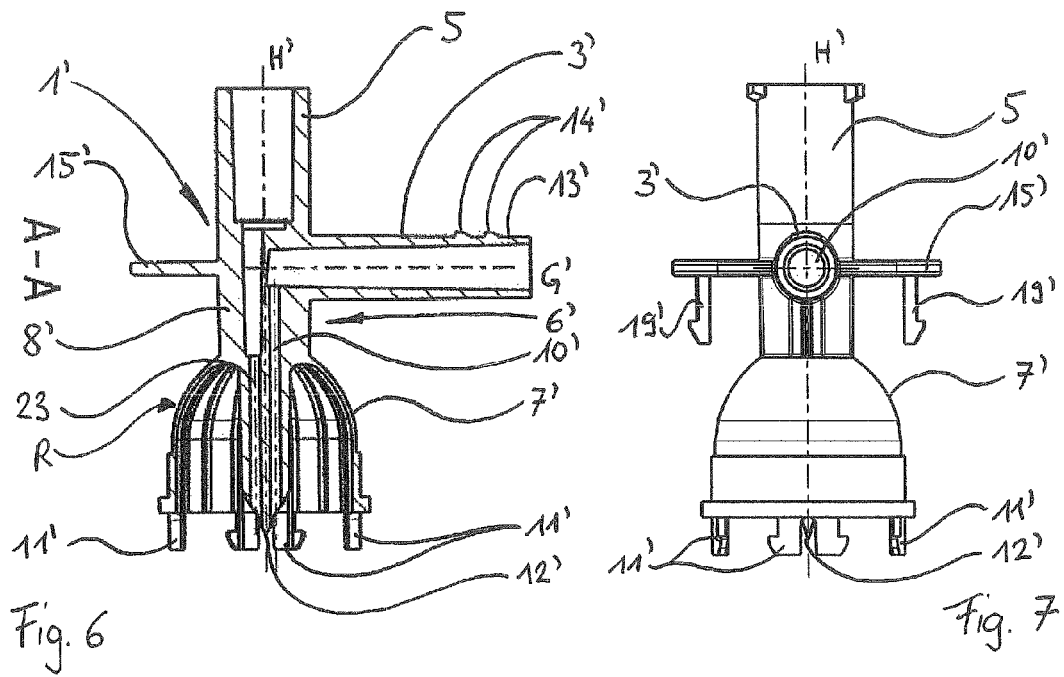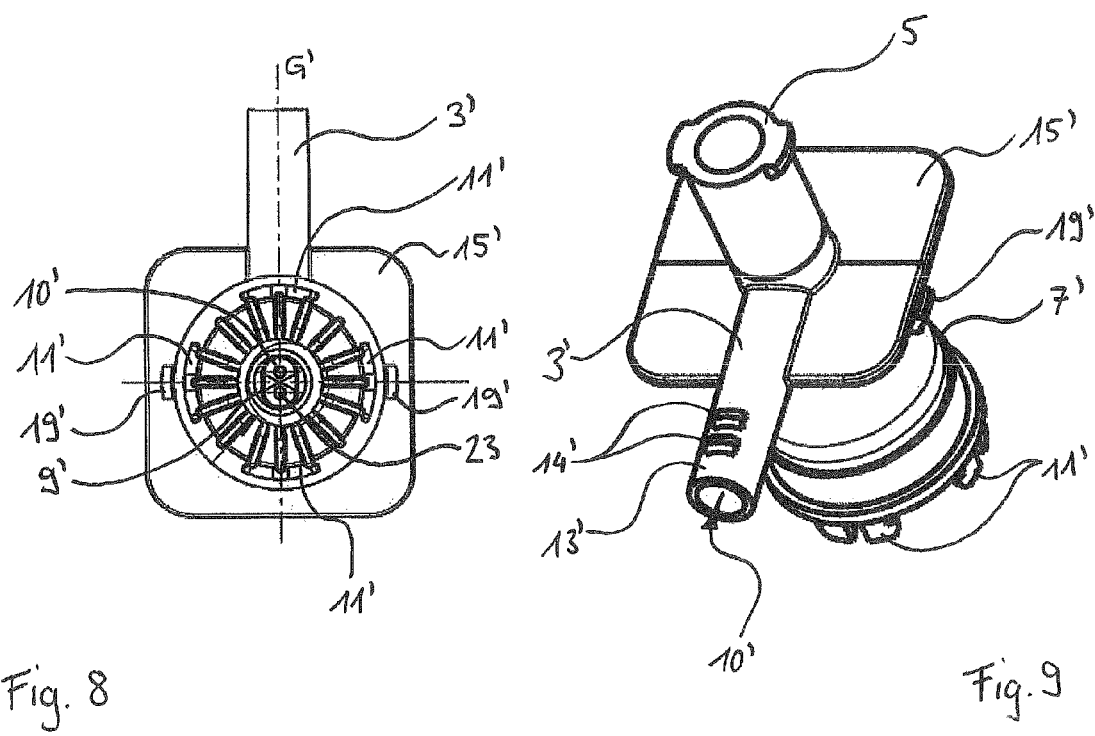

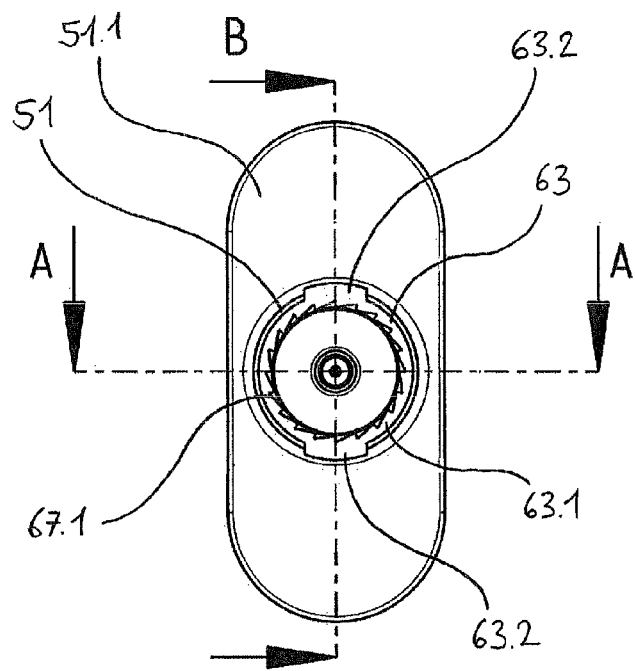
Fig. 21
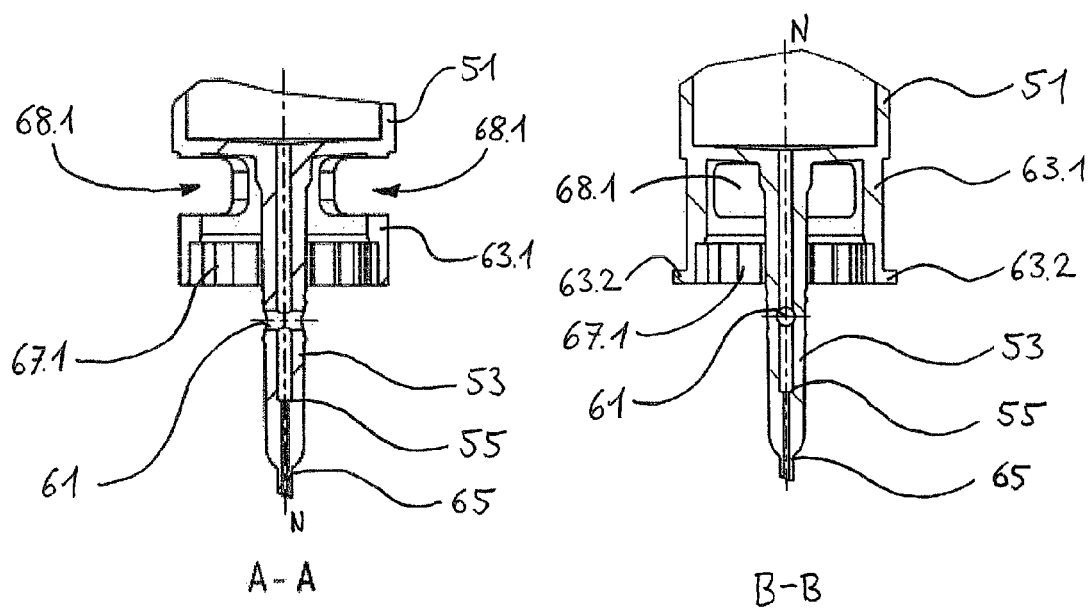
Fig. 22
Fig. 23

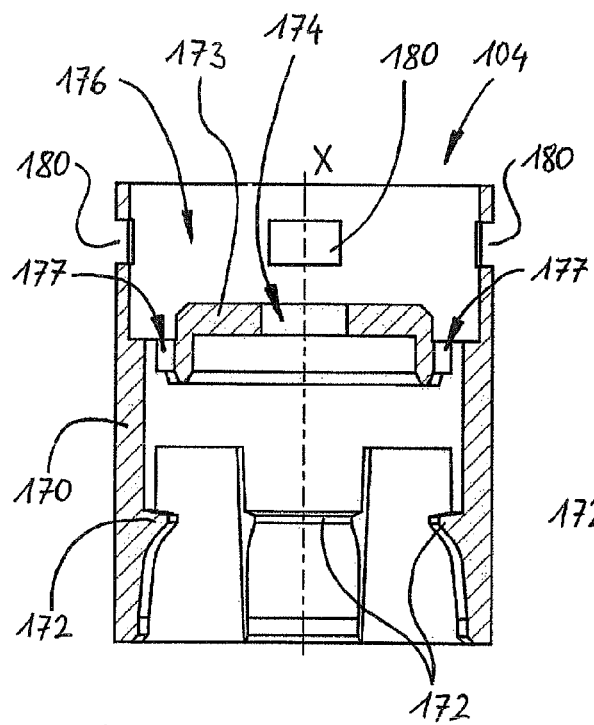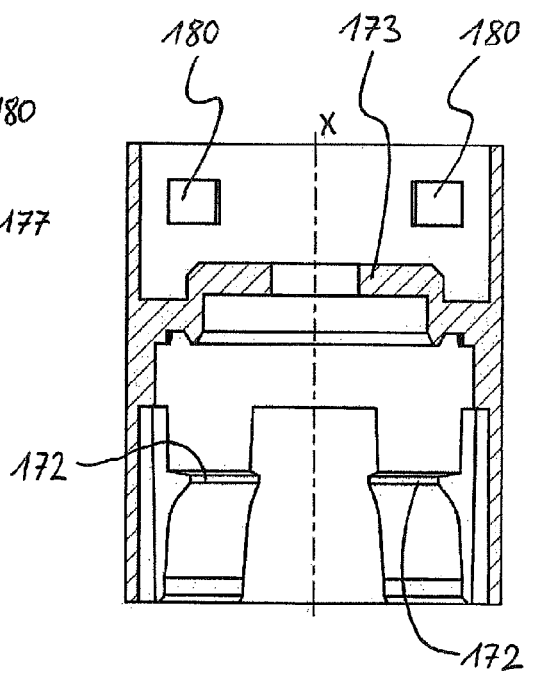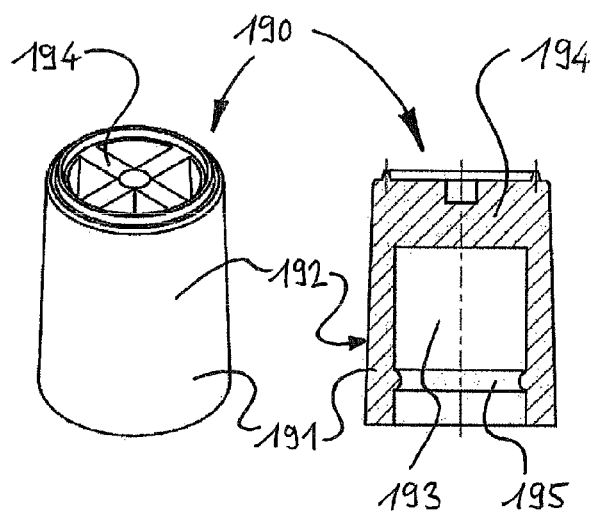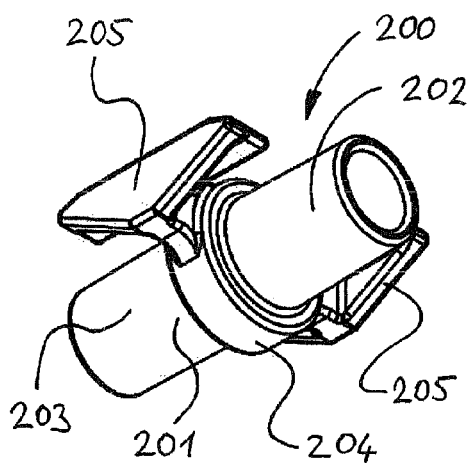
Fig. 30    Fig. 31    Fig. 32a    Fig. 32b    Fig. 33

ADAPTER FOR A TRANSFER DEVICE FOR A FLUID, AND TRANSFER DEVICE

The invention relates to an adapter for a transfer device for a fluid for connecting a container containing the fluid, according to the preamble of claim 1. The invention further relates to a transfer device formed from such adapters for a fluid from a container to a discharge device.

Such transfer devices are generally devices for the removal of pharmaceutical substances without needles from one or more hermetically sealed glass vessel(s). In particular, it is often necessary to mix different medical substances with each other or to dissolve different medical substances one in the other (for example, liquid/liquid or liquid/solid) only shortly before administration because they cannot be stored as mixture or solution. To this end, the different medical substances must be stored in separate containers and be mixed under sterile conditions before they are transferred to a discharge device, for example, an injection syringe. Such devices can naturally also be used in the non-medical field, for example, for chemical analysis purposes in the foodstuff sector or in the cosmetics sector.

Known devices for mixing and administering two medical substances comprise double-chamber syringes as disclosed, for example, in U.S. Pat. No. 4,424,057. They may be packaged in a ready-to-use state for single use, but have the disadvantage that they have a comparatively large structural length and are therefore difficult to store. It is further impossible to use medicament containers having standardized connection couplings but instead the syringe has to be filled individually.

WO 2009/146088 A1 discloses an adapter of a transfer device for a fluid which allows two standardized medicament containers, which are sealed with a penetrable sealing element, for example, of rubber, to be connected in order to mix two medical substances. To this end, the adapter has two oppositely arranged coupling locations for the containers each having at least one hollow needle for piercing the sealing element. The containers are snap-fitted in an engagement collar of the coupling locations, the hollow needles extending through the sealing element. The hollow needles can be connected to each other via fluid channels of the adapter in order to mix the medicaments. The connection to a connection port to which a syringe can be connected to draw up the mixture can be produced via a sliding member.

WO 2008/126090 A1 discloses a transfer device for a liquid medicament which has to be mixed with a solid or liquid medicament before administration. To this end, there is provided a coupling location having a hollow needle for a container which is sealed with a penetrable sealing element and which contains a liquid or solid medicament. Another liquid medicament is introduced by a syringe at a connection port and reaches the container via fluid channels of the adapter. Another port serves to discharge the mixed medicament. A closure tap allows the fluid-tight closure of the hollow needle in order to prevent dripping of the medicament mixture when the container is removed or changed.

A substantial disadvantage of known transfer devices having an adapter is that the containers can be fitted to the adapter only shortly before use. Therefore, a prefabricated and ready-to-use arrangement is impossible. For reasons of sterility and simpler handling, however, there is a need for providing a ready-to-use transfer device having container(s) and a discharge device in a sterile packaging so that for use only a small number of hand actions and in particular no connection of sterility-sensitive components are necessary in order to transfer the medical substance(s) to the discharge device.

Furthermore, there is generally the problem that transfer devices having an adapter have a comparatively large structural size with poor use of space when all the necessary components (transfer device, container, injection syringe) are arranged, and are only suitable for a ready-to-use arrangement to a small extent. As a result of the unfavorable arrangement, a packaging must further be selected to be particularly stable so that no damage occurs owing to mechanical effects. Furthermore, known transfer devices having an adapter for a container for a fluid are generally only provided for a specific configuration and as a result restricted in terms of application.

Therefore, an object of the invention is to provide a device of the type mentioned in the introduction in which the disadvantages mentioned are avoided and which particularly allows a compact construction method of a transfer device. The device is further intended to afford the possibility for a transfer device which can be used in a versatile manner. The device is further intended to allow transfer devices which operate in a reliable manner and are also simple to operate by operators who are not specially trained. It is further intended to be simple and cheap to produce because the device is a component of a disposable packaging which has to be disposed of after use.

Those objects are achieved according to the invention with a device which has the features of claim 1. The claim relates to an adapter for a transfer device for a fluid for connecting a container containing the fluid, wherein the container is sealed with a penetrable sealing element and the adapter has a cap member which can be positioned in a sealing manner in a positioning direction on a container opening which is sealed with the sealing element and on which a penetration element is supported in such a manner that the penetration element can be displaced by means of guide means between a rest position and a removal position, wherein the penetration element has a hollow needle, with which the sealing element can be penetrated in the removal position, wherein the adapter has a connection piece having a connection coupling for the fluid-tight connection of another adapter and a transfer channel extends from an opening in the connection piece as far as an opening in the hollow needle so that the opening of the transfer channel in the connection piece communicates with an inner space of a connected container in the removal position of the penetration element. The invention is distinguished in that the connection piece is arranged transversely, in particular substantially perpendicularly, relative to the positioning direction, preferably on the penetration element. The connection piece is preferably arranged with its longitudinal axis perpendicular relative to the positioning direction.

The adapter according to the invention allows a plurality of adapters to be coupled together in order to form a transfer device. As a result of the modularity achieved in this manner, therefore, versatile configurations of a transfer device are possible by combining a plurality of adapters. On the basis of the rest position of the penetration element, the adapter further allows a container to be arranged in a ready-to-use state on the adapter or a plurality of containers to be arranged in a ready-to-use state in a transfer device having a plurality of adapters which can be reliably activated only a short time before use readily by the penetration element being pressed in without any risk of contamination. As a result of the connection pieces which are arranged transversely, in particular perpendicularly, relative to the positioning direction, a compact structural size can further be achieved, whereby the ready-to-use arrangement is also particularly suitable, for example, for storing and transport.

The positioning direction of the adapter on the container generally corresponds to a longitudinal axis of the container, which is in the form, for example, of a glass vial. In this manner, a plurality of adapters may be arranged each with a container connected in the positioning direction, for example, parallel in either a unidirectional orientation or in an opposed (anti-parallel) orientation which is rotated through 180 degrees relative to an axis of the connection pieces. The latter arrangement is advantageous in particular in the event that one of the containers comprises a medicament in liquid form and the other container comprises a medicament in solid form which is intended to be dissolved in the liquid medicament before administration. An identically orientated (parallel) arrangement is particularly advantageous in the case of two liquids which are intended to be mixed directly before use.

As a result, different transfer devices can be produced with the same adapter according to the invention, which allows particularly versatile use. As a result of the arrangement of the connection piece in the transverse direction, in particular a total structural size of the transfer device can be substantially reduced because the adapters can be arranged, for example, in a state beside each other or offset relative to each other, in accordance with requirements and so as to be adapted to the dimensions of, for example, containers and the discharge device. Depending on requirements, the connection piece can to this end have different lengths which are adapted to the known dimensions of known containers so that it is possible to pack a plurality of containers as tightly as possible.

The cap member of the adapter can advantageously carry a centering ring which further guides and centers the hollow needle. The sealing element is thus penetrated at a precisely defined location. Furthermore, undesirable transverse movements owing to incorrect handling during injection are prevented. In the removal position, the penetration element is therefore also stabilized so that forces on a connection piece formed on the penetration element can be taken up partially by the cap member via the centering ring.

For further stabilization, the penetration element may further have engaging means with which it can be engaged in the removal position. It is thereby ensured that, when the fluid is removed or when the penetration element of another connected adapter is actuated, no undesirable relative movements occur.

Additional advantages can be achieved if the guide means have at least one wall portion which connects the penetration element to the cap member and retains it in the rest position, wherein the wall portion can be deformed in such a manner that it guides the penetration element until the removal position is reached. On the one hand, rotation prevention is ensured by the secure connection between the cap member and the penetration element but, on the other hand, good linear guiding as a result of the deformability is also ensured.

The deformable wall portion may be, for example, at least one resilient membrane which surrounds the penetration element. The membrane may be able to be deformed in such a manner that it fixes the penetration element in the removal position with resilient biasing. The membrane which is formed in a dome-like manner is consequently biased both in the rest position and in the removal position as a result of the resilient properties thereof. The "clicking" effect of the membrane is used. Naturally, however, engaging means may also be arranged to fix the penetration element in the removal position so that the resilient biasing of the membrane is insignificant for retaining the removal position.

The membrane may be constructed in quite different manners and, for example, may also comprise a plurality of mutually separate segments in a peripheral direction. In the removal position, atmospheric air can flow in via the intermediate spaces between the segments. However, it is also conceivable that a membrane closed in the rest position be provided with predetermined breaking locations which burst when the penetration element is moved into the removal position. Such predetermined breaking locations have the advantage that the membrane in the rest position is relatively dimensionally stable and has an increased level of resilience only after the bursting of the predetermined tearing lines. Furthermore, in this instance too air may flow in from the atmosphere via the burst predetermined tearing lines in the removal position.

Alternatively, however, the guide means may also have at least two webs which form the wall portions mentioned and each of which is provided with at least one bending member in such a manner that the webs can be folded together when the penetration element is displaced into the removal position. The webs thereby form spider-like legs of the penetration element, which legs can preferably be folded outward in the course of the linear movement.

Alternative configurations of the guide means would naturally be conceivable. For instance, the wall portion could, for example, also be in the form of a bellows which can be compressed in the manner of an accordion. It would also be conceivable to have a number of rings or ring segments which are connected to each other and which can be compressed in a telescope-like manner.

A substantial advantage is achieved in any case if the guide means are connected integrally to the cap member and/or to the penetration element. The entire structure can thereby be produced integrally as an injection-molded component from plastics material. In particular, it is also advantageous to produce the connection piece integrally with the penetration element.

In specific cases, however, it may also be advantageous in technical manufacturing terms to produce individual components separately and subsequently to weld them to each other or to connect them to each other in some other manner. In this case, for example, the guide means are preferably connected to the cap member via a snap-fit coupling. As a result, differently constructed guide means or penetration elements having formed-on guide means can readily be snap-fitted onto identically constructed cap members by means of a uniform coupling. As a result of the modular construction of the adapter itself achieved in this manner, the thrift of the adapter is further improved by using members of the same type for different configurations. Furthermore, different material properties can be paired with each other in an optimum manner. For example, materials which can be sterilized with a plurality of methods (for example, which can be sterilized with radiation or with steam), without becoming damaged are optimum.

Another very advantageous configuration involves selecting plastics materials which are as transparent as possible for the individual components of the adapter. The product which is completely filled and assembled can thereby be visually inspected for any defects without being destroyed.

A configuration of the adapter with a ventilation channel for ventilating the container when the fluid is removed is particularly advantageous. The at least one ventilation channel, which preferably extends along the hollow needle, causes the interior of the container to be short-circuited with respect to the atmosphere in the removal position. The production of a constantly increasing reduced pressure in the container is thereby avoided because as much air flows into the container as liquid is removed. As a result, a backflow of liquid into a container which is connected to the adapter can be prevented, with sterile conditions being maintained, when liquid is discharged via the transfer channel.

Naturally, it is conceivable to arrange a plurality of ventilation channels which can extend along the hollow needle either linearly or in a helical manner. It would also be conceivable to arrange a ventilation channel on an element which is separated from the hollow needle, for example, in the form of a separate ventilation needle.

Depending on requirements, in a preferred embodiment the ventilation channel may be in the form of an internal fluid channel. In this manner, the ventilation channel can be prevented from being able to be sealed by the penetrable sealing element in an undesirable manner.

Advantageously, however, the ventilation channel is in the form of a groove at the outer side of the hollow needle. There are preferably a plurality of parallel grooves. Such a component is simple to produce and, if the groove depth is sufficient, an adequately large passage cross section is kept free even if the sealing element comprises very soft and resilient material.

In spite of the ventilation channel, a dirt-free and even germ-free environment is ensured in the container if, according to another configuration, the supplied air has to pass a filter. In accordance with the quality of that filter, extremely small particles or micro-organisms can also be retained. Therefore, the adapter preferably comprises at least one filter via which air can be supplied in the removal position from the atmosphere to the container via the ventilation channel.

The filter may in principle be arranged on the penetration element and may be displaced therewith, or it may be retained rigidly on the cap member. The important aspect in each case is that the side of the filter facing the ventilation channel is a component of a space which is delimited in a sterile manner from the atmosphere. The filter may, for example, be arranged on the penetration element, preferably at the atmosphere-side end of the ventilation channel, for example, on a collar which surrounds the hollow needle and which is provided with openings and, at the same time, supports or carries the filter. This variant arranged near the ventilation channel has the advantage that the filter can be kept relatively small in terms of surface-area. Alternatively, however, the filter may also be arranged in a separate filter insert which, for example, can be inserted in a receiving space in the adapter, which space is provided therefore and communicates with the ventilation channel. For example, it may be advantageous to arrange the receiving space for the filter insert in a suction opening for the inwardly flowing air.

In the case of the filter being associated with the cap member, the arrangement is preferably brought about in a region facing the container opening. The filter may be arranged in a retention member which surrounds the penetration element in the manner of a circular ring if the penetration element is in the removal position. This arrangement has the advantage that the space which is intended to be kept sterile in the rest position can be kept very small.

Another embodiment of the adapter may comprise a coupling means for coupling a discharge device in a coupling direction. Discharge devices typically have an elongate construction similar to, for example, syringes of known construction type. The coupling direction in which the discharge device is coupled to the coupling means corresponds to the longitudinal direction of the discharge device. The adapter comprises an additional fluid channel which is in the form of a removal channel and which extends from an opening in the coupling means as far as an opening in the hollow needle. The removal channel extends in such a manner that, when the penetration element is in the removal position, the opening of the removal channel in the coupling means communicates with the inner space of a connected container. The coupling direction predetermined by the coupling means and the positioning direction of the container are advantageously orientated parallel with each other. The coupling means may comprise known couplings, preferably an inner cone of a Luer coupling.

The coupling means may be formed so as to be laterally offset on the adapter in relation to the coupling direction so that a needle or cannula fitted to the discharge device can extend parallel with and along the container. To this end, a sleeve for receiving the cannula or needle may be formed directly on the adapter, in particular on the penetration element. The fluid can be supplied in this case via a separate filling opening of the discharge device, for example, similarly to the embodiment of a coupling means having a tap system, which embodiment is described below.

In this embodiment of the adapter, no ventilation channel is typically necessary because it is provided to draw a fluid into the connected container in the transfer device via a reduced pressure at the coupling means, for example, by drawing a discharge device constructed as a syringe via the transfer channel. In the connected container, the fluid can mix with another fluid present therein or dissolve a solid substance present in the container. The mixture or the solution can then be removed via the removal channel or supplied to the discharge device.

In another alternative embodiment of the adapter, a second connection piece having a connection coupling for the fluid-tight connection of another adapter is provided. The second connection piece is arranged preferably transversely, in particular perpendicularly, relative to the positioning direction. In a particularly preferred manner, the longitudinal axes of the two connection pieces are in the same plane arranged transversely relative to the positioning direction. The adapter comprises an additional fluid channel which is in the form of a second transfer channel and which extends from an opening in the second connection piece as far as an opening in the hollow needle so that the opening of the second transfer channel in the second connection piece communicates with the inner space of the connected container.

This embodiment of the adapter is suitable for the connection of two additional adapters if, for example, more than two medicaments have to be mixed before administration.

In a transfer device, however, an adapter which is constructed only for the supply of one fluid to the discharge device can also be connected to all the above-mentioned embodiments of an adapter according to the invention. By a separate adapter being provided for connecting the discharge device, the adapter can be adapted to the specific requirements in a particularly good manner.

Such an adapter which is also advantageous in a state separated from the above-mentioned adapters comprises a coupling means for coupling a discharge device in a coupling direction which preferably corresponds to a longitudinal direction of the discharge device. The adapter comprises a connection piece having a connection coupling for an additional adapter, wherein a fluid channel extends continuously from an opening in the connection piece to a mouth opening in the coupling means. The connection piece is preferably arranged transversely, in particular perpendicularly, relative to the coupling direction and has a housing having a receiving space for, for example, a needle or cannula of the discharge device. The housing acts in the manner of known protective caps for injection needles.

As a result of the arrangement of the connection pieces selected similarly to the above-mentioned adapters for connecting a container, the adapter provided only for supplying a fluid to a discharge device can also advantageously be arranged in a transfer device in a versatile and space-saving manner.

The coupling means for the discharge device is preferably formed in the region of an outwardly open introduction opening of the receiving space, wherein the receiving space preferably extends substantially in the coupling direction. The mouth opening is arranged in such a manner that a filling opening of the discharge device can be connected to the mouth opening of the fluid channel in a fluid-tight manner when the discharge device is coupled.

In particular, the coupling means comprises an inner cone, wherein the mouth opening is arranged on lateral surface of the inner cone. In the case of a correspondingly constructed discharge device, that is to say, in the case of a discharge device having a corresponding outer cone acting as a complementary coupling means, the filling opening is arranged on the lateral surface of the outer cone. The filling opening is preferably provided in addition to a discharge opening. The advantage is connected with the fact that, for example, the discharge device can be filled via the separate filling opening when a cannula or needle is inserted in the discharge opening.

A discharge device which is particularly suitable for this embodiment of the adapter is described below. In particular, the discharge device described below may already be provided with the adapter, whereby, for example, an injection needle is protected in the receiving space and the discharge device can be filled via the connection piece of the adapter.

However, it will be understood that other discharge devices which can be filled via a discharge opening provided for discharging a fluid are also suitable for this embodiment of the adapter. In this instance, the opening of the fluid channel at the coupling means is arranged in accordance with the position of the discharge opening of the discharge device.

However, a particularly preferred embodiment of a discharge device which can also be advantageously used in a state separated from the adapters described here or transfer devices which comprise such adapters comprises a separate filling opening. However, a separate filling opening is generally problematic or complex to the extent that it also has to be sealed separately in order to ensure that the fluid is discharged through a discharge opening of the discharge device. The discharge device described below solves this problem in a structurally simple manner which is reliable and simple to operate.

Such a discharge device for a fluid comprises a base member having an inner space for receiving the fluid, wherein a discharge opening which communicates with the inner space via a fluid channel and at which the fluid can be discharged where necessary is formed in a discharge region. A coupling means for coupling the discharge device to a transfer device for a fluid is formed in the discharge region and can be introduced into a correspondingly formed coupling means of the transfer device for coupling in a coupling direction. The coupling means of the discharge device has a filling opening which communicates in a fluid-linked manner with the inner space in a filling position of the discharge device and via which the discharge device can be filled with the fluid. The coupling means is constructed in such a manner that the fluid linkage between the filling opening and inner space of the base member can be interrupted. The discharge device is distinguished in that the coupling means of the discharge device is supported on the base member so as to be rotatable about a rotation axis which is orientated in the coupling direction and the fluid linkage between the filling opening and the inner space can be interrupted as a result of such a relative rotation between the base member and the coupling means.

Such a discharge device can generally be connected to a filling or transfer device provided with a corresponding coupling means. However, the discharge device is described below in connection with an adapter for a transfer device without limiting the general applicability.

The discharge device preferably has engaging means which are securely formed on the base member and which are engaged with corresponding engaging means on the adapter, in particular in a bayonet-like manner, in order to secure the coupled discharge device. The bayonet-like engagement can consequently be easily released by the base member of the discharge device being rotated relative to the adapter about an axis corresponding to the coupling direction.

The coupling means of the discharge device preferably has means for rotationally secure retention in the coupling means of the adapter. As a result, it is ensured that the base member is also rotated relative to the coupling means of the discharge device in the event of a rotation of the base member relative to the adapter when the discharge device is coupled. In this manner, on the one hand, the fluid linkage between the filling opening and the inner space can be interrupted as a result of the rotation of the base member relative to the adapter. On the other hand, the engagement of the bayonet-like engaging means of the base member with the engaging means of the adapter may optionally be released at the same time so that the discharge device is disengaged and can be uncoupled from the adapter. The means for rotationally secure retention may comprise grooves or ribs which are arranged in the coupling direction so that the coupling means can be moved into/out of the coupling means of the adapter in this direction.

The filling opening is preferably constructed laterally on the coupling means of the adapter device in relation to the coupling direction so that the filling opening can be connected in a fluid-tight manner to a transfer opening of a fluid channel, which opening is formed accordingly in the adapter.

The coupling means of the discharge device is advantageously in the form of a cuff which is supported on a cap member connection piece arranged on the base member in the coupling direction. The filling opening is advantageously formed on a lateral surface of the cuff. In particular, the filling opening is formed on a conical portion of the lateral surface in order to readily ensure a fluid-tight coupling in a correspondingly conical seat of the coupling means of the adapter.

The cap member connection piece is preferably arranged on the base member in the longitudinal direction of the base member, wherein the discharge opening is arranged at the front side on a longitudinal end of the cap member connection piece, which end is directed away from the base member, and the fluid channel extends in the cap member connection piece from the discharge opening to the inner space.

The fluid linkage between the filling opening and the inner space is advantageously produced by means of a transverse hole in the coupling means and in the cap member connection piece, respectively, which are arranged and formed in such a manner that they are aligned with each other in the filling position of the discharge device. The transverse hole in the cap member connection piece communicates with the fluid channel of the discharge device. The term "transverse hole" is intended here and below to refer to a hole which is transverse relative to the coupling direction or rotation axis of the coupling means. The inner fluid channel of the connection stud opens at a longitudinal end facing away from the receiving space in a discharge opening provided to discharge the fluid from the receiving space. As a result, the filling opening is arranged in a lateral region independently of the discharge opening, whereby the discharge device can be filled, for example, when the needle or cannula is positioned or when the discharge opening is sealed. A direct inference of this is that the hygienically most relevant region, that is to say, the discharge region or an injection needle or cannula, does not have to be directly manipulated by a user in order to close the filling opening.

In order to ensure only one-time usability of the discharge device, there are preferably provided securing means which allow rotation of the base member in relation to the coupling means of the discharge device only in an uncoupling direction, in particular only in a limited range. Engaging tongues by means of which rotation counter to the uncoupling direction can be blocked in the manner of a ratchet are preferably constructed for this purpose. Stops which limit rotatability to a specific angular range may also advantageously be provided. The securing means are preferably formed on the coupling means of the discharge device and cooperate with elements fixed to the base member, in particular, for example, with the above-mentioned engaging means of the base member.

A direct inference is that a discharge device provided with such a coupling means which is rotatably supported on the base member can be used in a versatile manner and clearly has advantages with regard to sterility requirements, construction and handling. In particular, correct and only one-time use of the discharge device can also be ensured.

The discharge device can advantageously be used in the case of correspondingly formed, above-mentioned adapters or a transfer device comprising such adapters (see below). In particular, a correspondingly formed coupling means having an opening for supplying fluid to the filling opening of the discharge device can be provided in all the adapters which are described here and which have coupling means for coupling a discharge device so that the discharge device can be coupled and filled accordingly. In particular, the discharge device may be arranged in a transfer device described herein in an adapter which is formed accordingly.

Another aspect of the invention comprises an arrangement which comprises at least two adapters and which provides a transfer device, in particular a modular transfer device, for the transfer of a fluid from a connectable container to a couplable discharge device, in particular to a discharge device which is described above and which has a separate filling opening.

The transfer device comprises at least one of the above-mentioned adapters having a ventilation channel and a second of the above-mentioned adapters having a coupling means for coupling a discharge device in a coupling direction.

The at least two adapters are connected to each other or secured to each other directly or indirectly in the transfer device via the connection couplings of the connection pieces in such a manner that, when a container or containers is/are connected, a fluid-tight channel is provided completely from the coupling means of the second adapter as far as the ventilation channel of the first adapter. If a reduced pressure is produced in the discharge device, for example, when a coupled syringe is drawn up, the fluid can flow from the container at the first adapter via the second adapter to the discharge device. The ventilation channel of the first adapter allows inward flow of air, which may optionally be filtered in a germ-free manner, from the atmosphere.

In accordance with the construction of the second adapter, the fluid may be supplied to the coupling means or the discharge device in the second adapter directly via the fluid channel or indirectly via a container connected to the second adapter. In the latter case, there may be provided in the connected container another medicament which, for example, can be mixed with the first fluid (second fluid) or can be dissolved therein (solid substance).

The connection couplings of the two adapters are advantageously constructed so as to complement each other in such a manner that the second adapter can be connected to the first adapter directly in a fluid-tight manner.

Alternatively, the transfer device advantageously comprises a coupling member in such a manner that the second adapter can be connected to the first adapter indirectly in a fluid-tight manner via the coupling member. In this manner, different adapters for different connection configurations do not have to be provided in the transfer device. The coupling member can be adapted in such a manner that each adapter can be connected to each other adapter, respectively. This has the advantage that adapters constructed in the same manner can be used with regard to the connection couplings.

In a particularly advantageous manner, the connection couplings of the two adapters are constructed in such a manner that the adapters can be coupled to each other in precisely two relative orientations, wherein the connection direction of the first adapter and the coupling direction of the second adapter are preferably opposed in one of the two orientations and are preferably aligned in the other orientation. Mutually complementary engaging means, which particularly, on the one hand, predetermine the orientations of the two adapters and preferably, on the other hand, secure the connection of the two adapters produced by the two connection couplings, are constructed on the connection couplings to this end.

As already mentioned in the introduction, the advantage that different relative arrangements of the adapters, and therefore of the connected containers, are allowed in the transfer device is connected therewith. Depending on whether two liquid medicaments are provided for mixing (preferably parallel arrangement) or a solid medicament is intended to be dissolved in a liquid medicament/solvent (preferably anti-parallel arrangement), the transfer device can be adapted to requirements in an optimum manner by corresponding relative arrangement of the adapters in the transfer device or the arrangement thereof in relation to a coupled discharge device.

In particular, however, a total construction size of the transfer device can be substantially reduced because the adapters can be arranged in accordance with the requirements and so as to be adapted to the dimensions of, for example, containers and the discharge device. By two orientations being provided, in which the relevant longitudinal directions (positioning direction, coupling direction) are arranged in a parallel or anti-parallel manner, a particularly compact construction can be achieved.

Naturally, in the event of indirect connection of two adapters via a coupling member, a corresponding orientation may be predetermined, for example, via the coupling member.

In a particularly advantageous manner, one of the connection couplings of the two adapters comprises an outer cone and the other of the two connection couplings comprises an inner cone, wherein particularly the inner cone is formed on the connection coupling of the first, ventilated adapter. As a result, it is readily possible to produce an assembly of two adapters with good fluid-tightness.

In the event of indirect connection via a coupling member, both connection couplings may have the same cone, wherein the coupling member has cones which correspond accordingly.

The transfer device may also comprise, in addition to the first and second adapter, at least one additional adapter which is provided with two connection pieces as described above. The connection coupling of the first connection piece is preferably constructed so as to complement the connection coupling of the first adapter and the connection coupling of the second connection piece is preferably constructed so as to complement the connection coupling of the second adapter so that the additional adapter can be connected simultaneously to the first adapter and second adapter directly in a fluid-tight manner. In this instance, the additional adapter is connected between the first and second adapters in terms of fluid to an extent.

It will be understood that, depending on requirements, the at least one additional adapter can also advantageously be connected to the first and/or second adapter indirectly via a coupling member.

Possible arrangements of the adapters comprise, for example, in a state assembled in the sequence mentioned in terms of fluid: an adapter having a ventilation channel, an adapter having two connection pieces and an adapter which is constructed only for supplying a fluid to the discharge device. The connection pieces are arranged with their longitudinal axes preferably in a common plane, wherein the connection pieces of the adapter can be arranged with two connection pieces at an angle relative to each other in such a manner that a triangular arrangement of the three adapters one beside the other is produced.

In order to protect the transfer device, for example, from mechanical damage during transport, there may be provided for protection a common housing in which the adapters of the transfer device are arranged. The housing can be constructed in such a manner that a coupled discharge device can also be received therein. The adapters are arranged in the housing in a configuration provided for use and can be secured in the relative positions. The housing may have access openings, through which the penetration elements of the individual adapters can be brought into the removal position and/or a coupled discharge device can be actuated.

In particular, the housing may also have securing means which predetermine correct handling of the transfer device. For example, the securing means may be constructed in such a manner that a correct sequence of the actuation operations is predetermined. The securing means may be constructed, for example, in such a manner that, in the event of two medicament containers, drawing of the discharge device can be carried out only when the penetration elements of the two adapters are in the removal position. Furthermore, there may also be provided securing means which ensure that the transfer device is used only once. However, the securing means may also comprise corresponding indications which are printed or stamped on the housing.

Additional advantages and individual features of the invention are illustrated in the drawings and are described below. In the schematic drawings:

FIG. 1 is a cross section through an adapter having a ventilation channel;

FIG. 2 is a top view of the adapter according to FIG. 1 in the direction of the axial connection piece;

FIG. 3 is a top view of the adapter according to FIG. 1 from a connection side;

FIG. 4 is a detailed view of the hollow needle having a ventilation channel of the adapter according to FIG. 1;

FIG. 5 is an external, oblique view of the adapter according to FIG. 1;

FIG. 6 is a cross section of another embodiment of an adapter having a coupling means for a discharge device;

FIG. 7 is a top view of the adapter according to FIG. 6 in the direction of the axial connection piece;

FIG. 8 is a top view of the adapter according to FIG. 6 from a connection side;

FIG. 9 is an external, oblique view of the adapter according to FIG. 6;

FIG. 21 is a top view of a base member of the discharge device according to FIG. 17 without any cuff;

FIG. 22 is a cutout of a longitudinal section of the base member according to FIG. 21;

FIG. 23 is a cutout according to FIG. 22 in a plane of section which is perpendicular to the view of FIG. 22;

Figure 24:
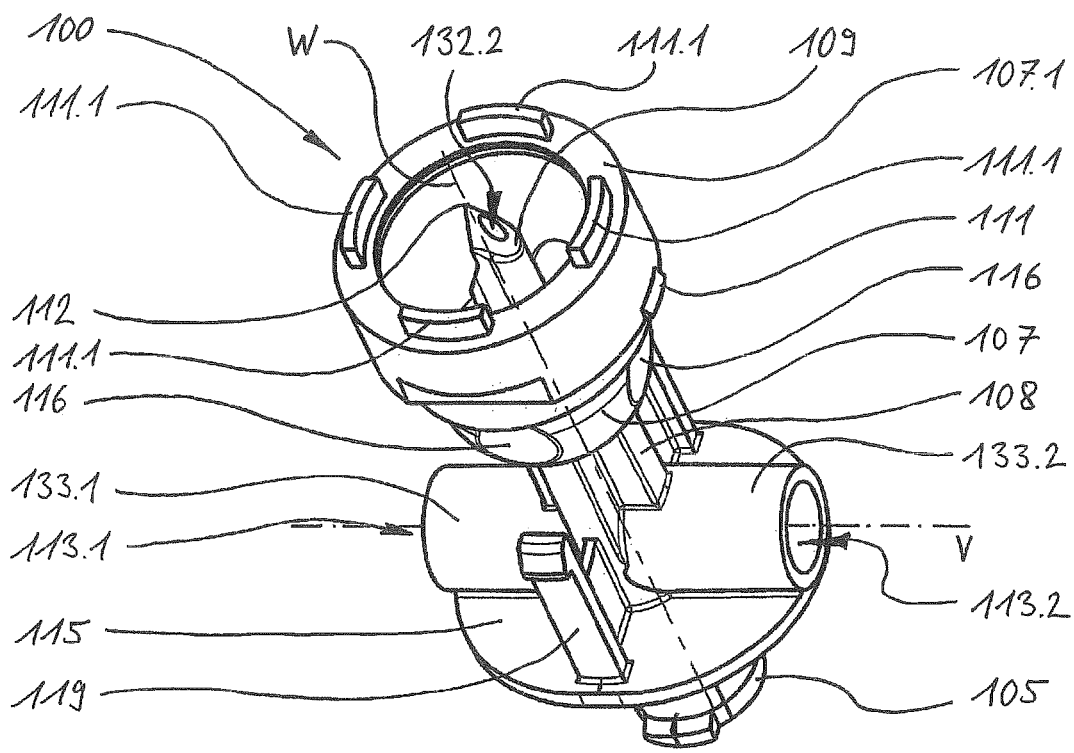
FIG. 24 is an external, oblique view of another embodiment of an adapter according to the invention.
Figures 28A, 28B, 28C:
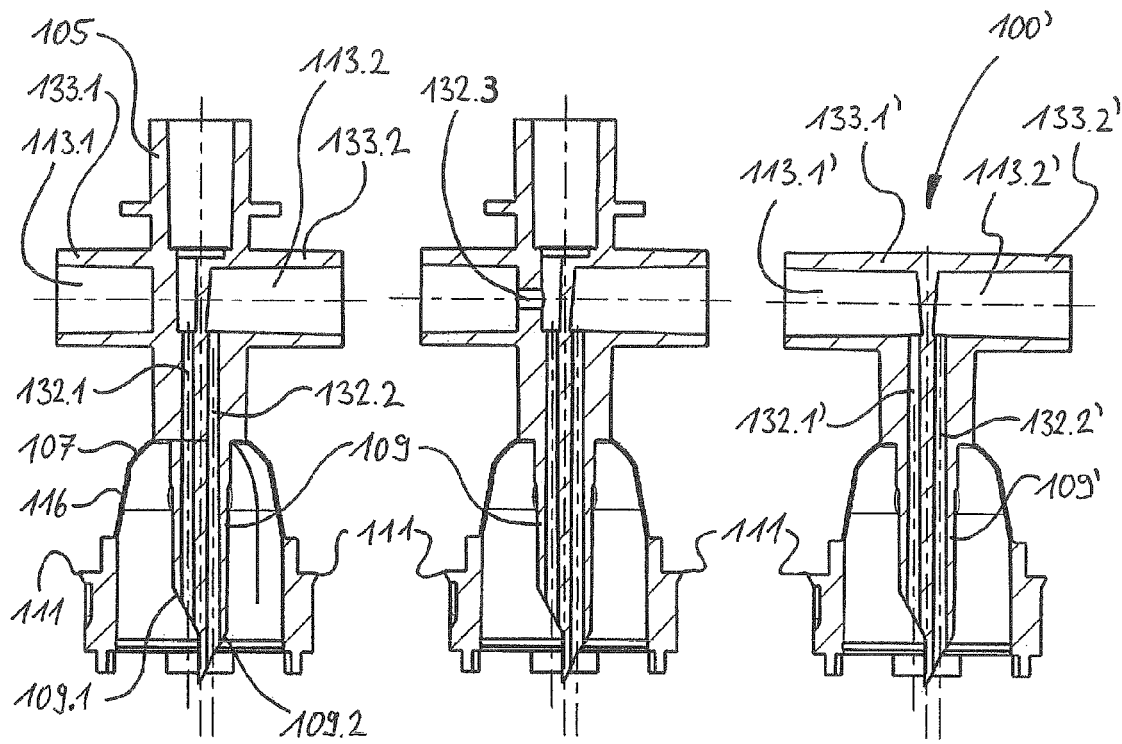
Figure 29:
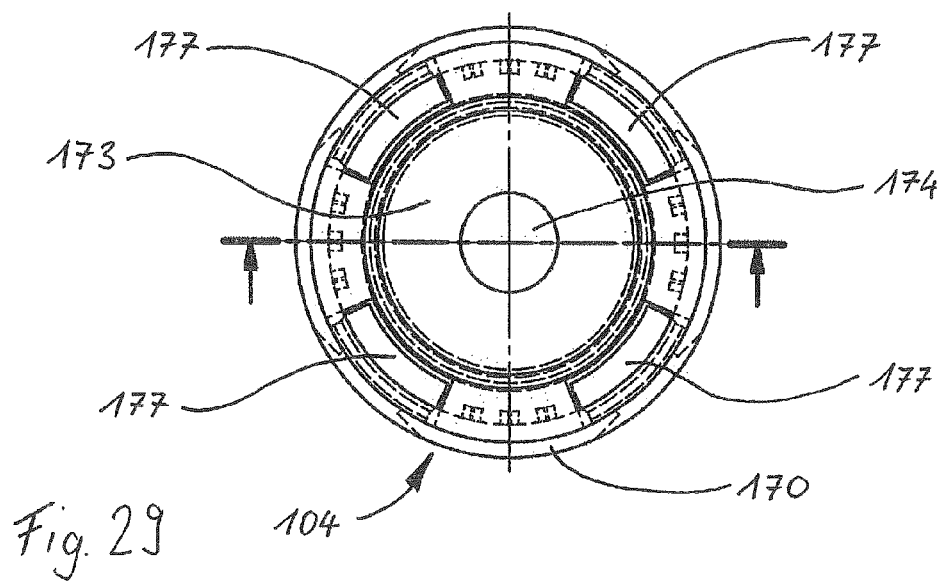

FIG. 28*a* is a longitudinal section through the adapter of FIG. 24;

FIG. 28*b* is a longitudinal section through the adapter of FIG. 24 with an alternative fluid channel guide;

FIG. 28*c* is a longitudinal section through another embodiment of an adapter according to the invention;

FIG. 29 is a top view of another embodiment of a cap member for the adapter of FIG. 24 in the longitudinal direction from a coupling side;

FIG. 30 is a longitudinal section through a cap member according to FIG. 29;

FIG. 31 is another longitudinal section through a cap member according to FIG. 29;

FIG. 32a shows a filter insert for an adapter according to the invention;

FIG. 32b is a cross section of the filter insert according to FIG. 32a;

FIG. 33 shows a coupling member for connecting two adapters according to the invention.

Components which correspond to each other are referred to below with the same reference numerals.

FIG. 1 is a cross section in a plane A according to FIG. 3 through an adapter 1 according to the invention having a ventilation channel 2 (see FIGS. 3 and 4). FIG. 2 is a front view and FIGS. 3 and 4 are views from a side provided for positioning on a container 17 but without a cap member 4 of the adapter 1, which cap member is in the form of a separate component in this instance. FIG. 5 is an external oblique view of the adapter 1. FIGS. 1 to 5 are described together below. The plane of section A is arranged perpendicularly relative to an axis G of a connection piece 3 and comprises a straight line H which designates a positioning direction of a container 17. The positioning direction is defined by means of a direction in which a container 17 is positioned on the adapter 1 and generally corresponds to a longitudinal direction both of the container 17 and of the adapter 1.

The adapter 1 comprises the cap member 4 (broken lines) which comprises plastics material and which is positioned on the outer edge region of the container 17 with the lower side thereof in a sealing manner. The container 17 is sealed by a penetrable sealing element 18 and also schematically indicated in FIG. 1 (broken lines).

The adapter 1 further comprises a penetration element 6 having a central base member 8. The base member 8 can be connected to the cap member 4 via a membrane 7 which is curved in a dome-like manner. In this instance, the membrane 7 comprises to this end snap-fit couplings 11 which are at the cap member side and which can snap-fit in corresponding recesses in the cap member 4. The cap member 4 is illustrated and described in detail in FIGS. 13 and 14. The penetration element 6 comprises a hollow needle 9 which extends from the base member 8 in the direction H in the direction toward the cap member 4. An internal fluid channel 10 extends along the hollow needle 9 and opens at a piercing tip 12 of the hollow needle 9, which tip 12 is provided with openings. The term "hollow needle" is used in this instance for any element which forms a drawing channel and which is capable of penetrating the sealing element.

As can also be seen in particular in FIGS. 3 and 4, the hollow needle 9 has a relatively thick wall, along which preferably parallel ventilation channels 2 are arranged in the form of grooves. Those grooves preferably extend substantially over the entire length of the hollow needle 9 from the piercing tip 12 as far as the base member 8. The entire penetration element 6 is preferably constructed integrally. It may be welded or snap-fitted in the membrane 7 or it may even also be constructed integrally with the membrane. The ventilation channels 2 may also be constructed as a dovetail groove in cross section. As a result, it is possible to reduce the risk that the resilient material of the sealing element seals the ventilation channels 2.

The penetration element 6 further comprises the connection piece 3 which extends away from the base member 8 in the direction G perpendicular to the positioning direction H. In this instance, the connection piece 3 is formed integrally on the penetration element 6. The connection piece 3 comprises a receiving space 13 for coupling a connection piece 3' of another adapter 1' (see FIGS. 6 to 9). The fluid channel 10 of the hollow needle 9 continues as far as the receiving space 13 and opens therein. An engaging recess 14 for an engaging means 14' of the connection piece 3' is formed in a wall of the connection piece 3. A corresponding engaging recess 14.1 may be formed opposite with respect to G so that the connection piece 23 can engage in a second orientation in the receiving space 13 of the connection piece 3, which orientation is rotated through 180 degrees (see FIG. 10).

As can be seen in FIGS. 2, 3 and 5, the penetration element 6 comprises an actuation plate 15 which is arranged perpendicularly to H and in which the connection piece 3 is arranged. The actuation plate 15 comprises downwardly protruding engaging means 19 which engage in a removal position E of the penetration element 6 at corresponding recesses of the cap member 4 (see FIG. 3).

The membrane 7 is constructed in a resilient manner so that it biases the penetration element 6 upward in the rest position R illustrated. Stabilization strips 16, which extend from the base member 8 along meridians on the dome-like membrane 7 and which reinforce it selectively are formed at the inner side on the membrane 7.

The removal of the liquid from a container 17 connected to the adapter 1 in the removal position E is explained below (not illustrated). In order to move into the removal position E, a force is applied in the direction K to the penetration element 6, for example, by means of the base member 8 or the actuation plate 15. The penetration element 6 is moved toward the cap member 4, wherein the resilient membrane 7 becomes deformed. Where applicable, the membrane 7 bursts along meridian predetermined breaking lines provided therefore. If the penetration element 6 is pressed completely toward the cap member 4, the hollow needle 9 penetrates through the sealing element 18 of the container 17 so that the piercing tip 12 protrudes into the interior of the container 17 with the openings formed therein. The ventilation channels 2 further provide a connection between the inner space of the container 17 and an inner space delimited by the membrane 7.

In the removal position E, the membrane 7 is curved so powerfully in the direction of the sealing element 18 that the resilient biasing changes the force direction and fixes the penetration element 6 in the removal position E. The friction between the hollow needle 9 and the sealing element 18 further contributes to the fact that the penetration element 6 remains in this position. Furthermore, the engaging means 19 engage with the cap member 4 and fix the penetration element 6 in the removal position E.

The actual removal of the liquid does not occur in the position illustrated but instead in the inverted position so that the liquid in the container floods the opening of the fluid channel 10 at the piercing tip 12 of the hollow needle 9. By a reduced pressure being produced in the receiving space 13 of the connection piece 3, for example, by drawing up a connected syringe, liquid can consequently be drawn from the container 17 into the receiving space 13. The reduced pressure which is produced in the container 17 above the liquid level is compensated for by inflowing air from the atmosphere, which air reaches the container 17 via the ventilation channels 2.

FIGS. 6 to 9 illustrate an alternative embodiment of an adapter 1'. For the sake of greater clarity, an illustration of an associated cap member 4' and a connected container 17' has been dispensed with in FIGS. 6 to 9. FIGS. 6 to 9 are described together below. Components which correspond to each other are referred to with the same reference numerals with a prime symbol (').

The connection piece 3' which differs from the connection piece 3' of the embodiment of FIGS. 1 to 6 is formed on a base member 8' of a penetration element 6'. The connection piece 3' is longer than the connection piece 3 and does not have a receiving space. Instead, a fluid channel 10' of a hollow needle 9' continues along the connection piece 3' in the longitudinal direction thereof, that is to say, in the direction G', wherein a cross section of the fluid channel 10' is widened in the connection piece 3'. The outer dimensions of the connection piece 3' in an end region 13' substantially correspond to the inner dimensions of the receiving space 13 of the connection piece 3 so that the connection piece 3' can be formed in the receiving space 13 in an outwardly fluid-tight manner. The connection piece 3' further has engaging projections 14' which can engage in the recess 14 for engagement (see also in this regard FIG. 10). The receiving space 13 of the connection piece 3 and the end region 13' of the connection piece 3' consequently form mutually complementary connection couplings of the two adapters 1 and 1'.

An inner cone of a Luer lock 5 is arranged on the base member 8' so as to project upward, that is to say, directed in a direction counter to the hollow needle 9' away from the base member 8'. It will be understood that any type of coupling may also be provided for coupling a discharge device. The inner cone acts as a coupling means for coupling a discharge device, such as, for example, an injection syringe (see, for example, FIG. 10). The coupling means sets out a coupling direction H', in which a discharge device can be coupled.

The coupling direction H' coincides in this instance with a positioning direction of a container 17' (see FIG. 10), and is preferably generally arranged parallel therewith. The positioning direction generally also corresponds to a longitudinal direction both of the container 17' and of the adapter 1'.

A fluid channel 23 which extends as far as openings at the piercing tip 12' of the hollow needle 9' opens in the inner cone 5. Consequently, the hollow needle 9' does not have, in contrast to the illustration in FIGS. 1 to 5, any ventilation channels but does have two internal fluid channels 10' and 23.

Figure 10:
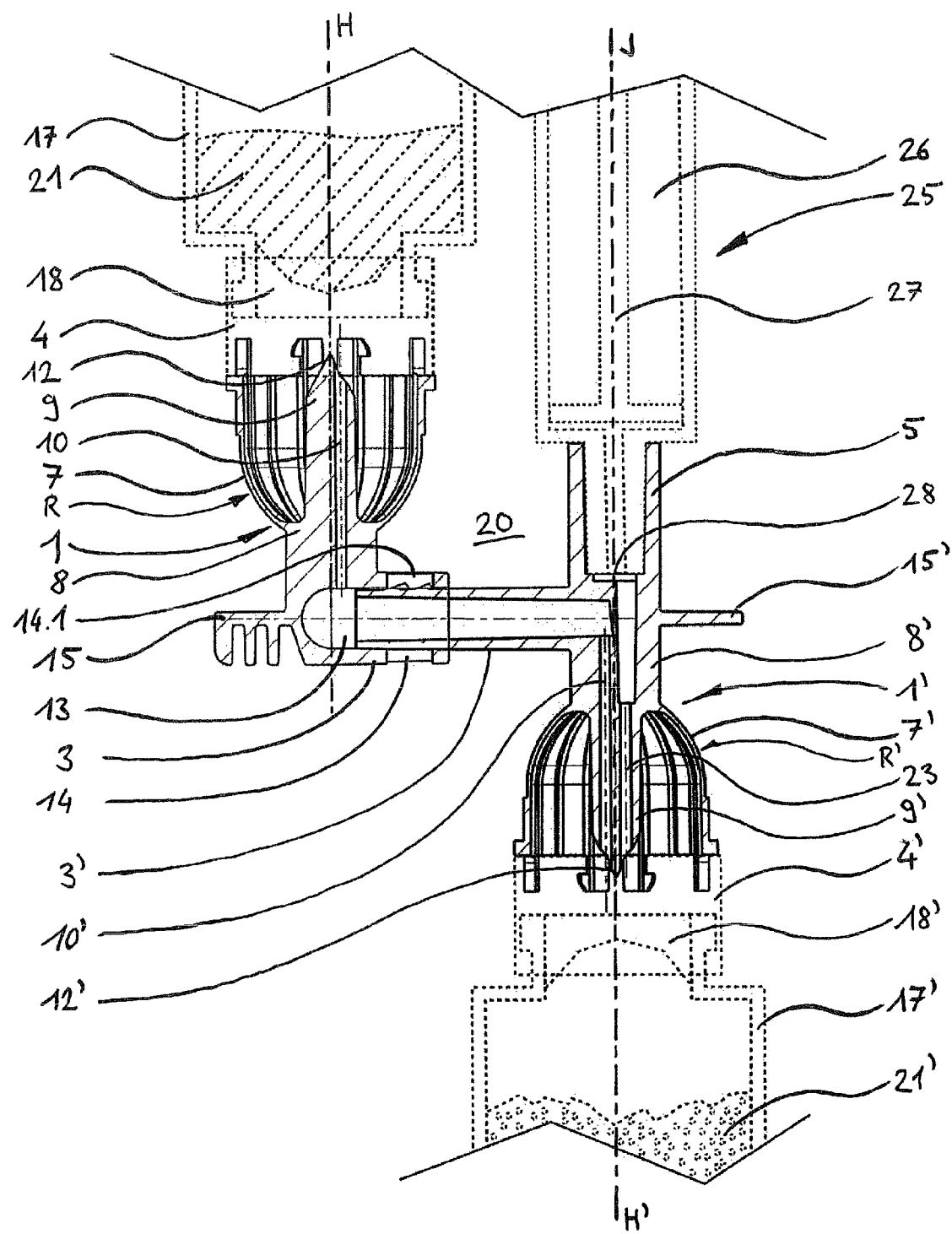
FIG. 10 shows the transfer device having a coupled discharge device and connected containers, with the containers being arranged in an anti-parallel manner.

The fluid channel 23 acts in this instance as a removal channel for removing a liquid from a container 17' connected to the adapter 1' (see FIG. 10). The actual removal of the liquid is also carried out in this instance not in the position illustrated, but instead in the inverted state so that the liquid in the container floods the opening of the fluid channel 23 at the piercing tip 12' of the hollow needle 9'.

FIG. 10 shows a transfer device 20 which is composed of an adapter 1 and an adapter 1'. A container 17 which contains a liquid medical substance 21 is connected to the adapter 1 on the cap member 4. Another container 17' which contains a solid medical substance 21' is connected to the adapter 1' on a cap member 4'.

The two adapters 1 and 1' are connected to each other via their connection pieces 3 and 3'. The adapters 1 and 1' are orientated anti-parallel with each other with the associated positioning directions H and H', that is to say, in accordance with the arrangement, one of the connected containers is directed upward (container 17) while the other is directed downward in the opposite direction (container 17'). To this end, the adapters 1 and 1' are connected to each other in such a manner that the engaging projections 14' are engaged in the engaging recess 14.1.

A discharge device 25 is coupled to the Luer coupling 5. The coupling direction H' in which the discharge device 25 is introduced into the Luer coupling 5 corresponds to a longitudinal direction J of the discharge device 25. A tappet 27, which is arranged in an inner space 26 of the discharge device 25 and which can be displaced in the longitudinal direction J in a fluid-tight manner, is displaced completely forward toward a discharge opening 28 of the discharge device 25, which opening is arranged in an opening of the removal channel 23 in the cone of the Luer coupling 5.

The containers 17 and 17' are sealed and the penetration elements 6 and 6' of the two adapters 1 and 1' are in the rest position R or R', respectively. The transfer device 20 is consequently in a ready-to-use and storable state.

In order to use the arrangement, the penetration elements 6 and 6' of the two adapters 1 and 1' are moved into the removal position E and E' (not illustrated), respectively, in which the penetration elements 6 and 6' extend through the sealing elements 18 and 18', respectively. If the tappet 27 is subsequently displaced in the inner space away from the discharge opening 28, a reduced pressure is produced via the removal channel 23 in the container 17'. As a result of the reduced pressure, the liquid medicament 21 in the container 17, which medicament floods the opening of the fluid channel 10 in the arrangement shown, is drawn into the container 17' via the fluid channel 10 and the fluid channel 10' connected thereto. Air can flow inward from the atmosphere into the container 17 via the ventilation channel 2.

Consequently, the solid substance 21' can dissolve in the liquid 21 in the container 17'. If the dissolution process is finished, the entire device can be inverted so that the mixture in the container 17' floods the opening of the removal channel 23 at the piercing tip 12'. By drawing the tappet 27 out further, the mixture can be transferred into the inner space of the discharge device 25. In order to be used, the coupling of the discharge device 25 with respect to the Luer lock 5 can be released and, for example, an injection needle (not illustrated) can be positioned.

From the above, it is apparent that no hygienically difficult fluid connections have to be provided in the entire transfer and mixing process. The specific construction of the adapters 1 and 1' with the penetration elements 6 and 6' which can be displaced between a rest position R or R' and a removal position E or E', respectively, allows simple and secure actuation or activation of the ready-to-use transfer device 20. As is also apparent from FIG. 10, the transfer device 20 having containers 17 and 17' connected thereto has a compact structural size as a result of the transversely orientated connection pieces 3 and 3'; in particular the container 17 is arranged parallel with the discharge device which can further be fixed to a snap-fit cuff (not illustrated) on the container 17, for example, for stabilization during transport.

Figure 11:
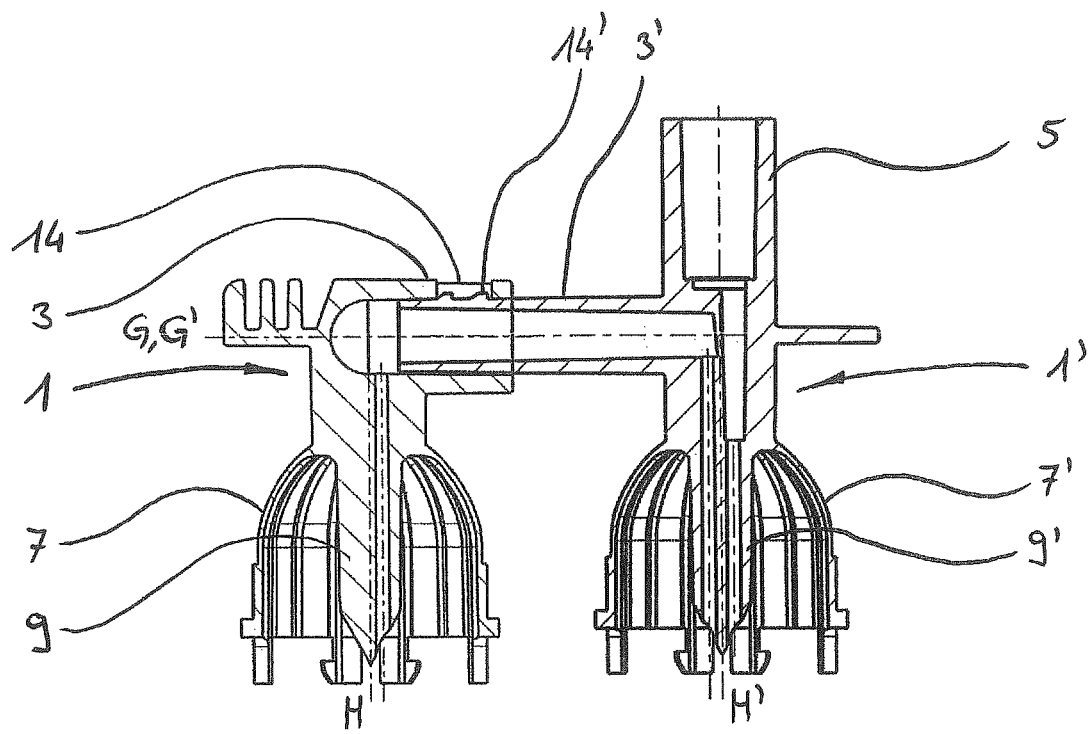
FIG. 11 shows a transfer device having an adapter arrangement for the parallel connection of two containers (adapters illustrated without cap members)

FIG. 11 shows the adapters 1 and 1' in an alternative configuration in which the positioning directions H and H' are orientated parallel (without any containers, cap members and discharge device). In this configuration, the engaging projection 14' is arranged in the recess 14, whereby an arrangement of the two adapters 1 and 1' relative to each other in a state rotated through 180 degrees in relation to the axis G/G' is produced.

This arrangement is advantageous for two liquids which are intended to be mixed directly before use. In order to use this arrangement, the penetration elements 6 and 6' of the adapters 1 and 1' arranged parallel are moved into the removal position E and E' (not illustrated), respectively. The actual removal of the liquids is carried out in the inverted state so that the liquids in the containers 17 and 17' flood the openings of the fluid channel 10 and 10' at the piercing tips 12 and 12'. If the tappet 27 is subsequently displaced in the inner space away from the discharge opening 28, a reduced pressure is produced in the container 17' via the removal channel 23. The liquid which is transferred from the container 17' into the discharge device 25 is compensated for with liquid from the container 17 because only in the container 17 air can flow inward from the atmosphere into the container 17 via the ventilation channel 2. During this operation, an advantageous mixture of the two liquids is produced during the transfer into the discharge device 25. Only when the container 17 is empty does the container 17' begin to empty itself since air from the atmosphere can flow inward via the container 17 into the container 17'. After the complete transfer of the liquids now mixed into the inner space of the discharge device, the coupling of the discharge device 25 with respect to the Luer lock 5 can be released for use and, for example, an injection needle (not illustrated) can be positioned.

Figure 12:
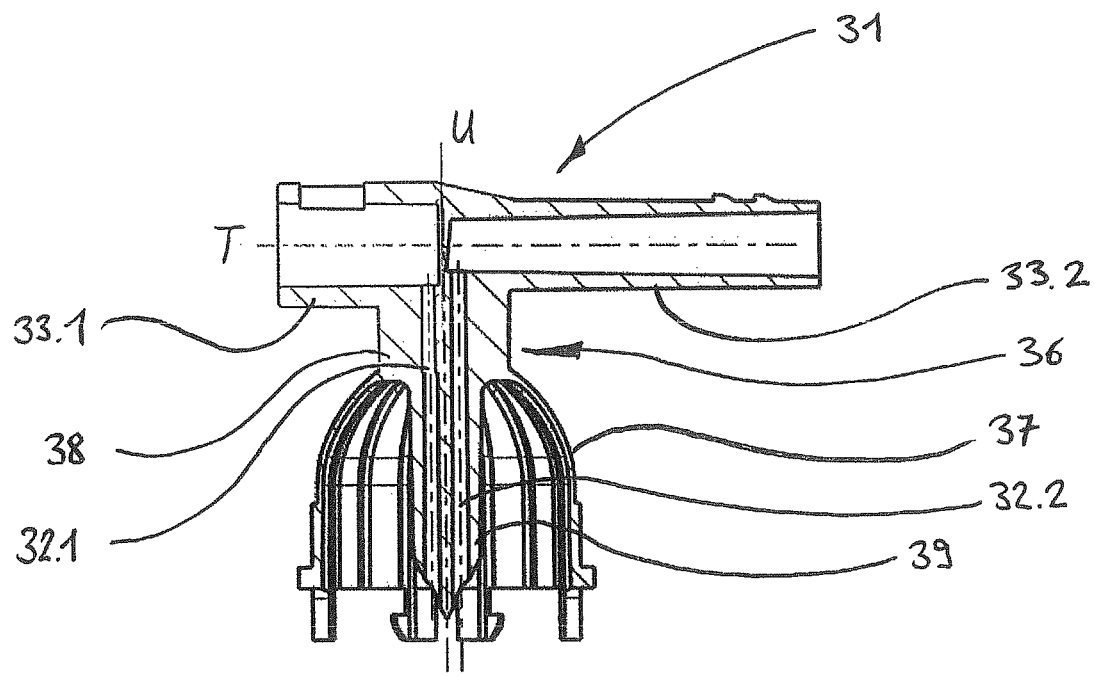
FIG. 12 shows another embodiment of an adapter as an intermediate piece, having two connection pieces (illustrated without cap member)

FIG. 12 shows a possible additional embodiment of an adapter 31 according to the invention. This adapter has two internal fluid channels 32.1 and 32.2 which are formed in a hollow needle 39 of a penetration element 36. The penetration element 36 has a base member 38 on which a first connection piece 33.1 and a second connection piece 33.2 are formed. The longitudinal axes of the two connection pieces 33.1 and 33.2 are on a common axis T, which is arranged perpendicularly to a positioning direction U of the adapter 31. It will be understood that the connection pieces 33.1 and 33.2 do not have to be arranged on a common axis but instead can also be arranged in relation to U at any angle such as, for example, 60 or 90 degrees. The formation of a resilient membrane 37 as a guide means of the penetration element 36 corresponds, for example, to the membrane 7 of the adapter 1.

The connection piece 33.1 is formed similarly to the connection piece 3 of the adapter 1, wherein a receiving space communicates with the fluid channel 32.1. However, the connection piece 33.2 is formed in accordance with the connection piece 3' of the adapter 1', wherein the fluid channel 32.2 continues in the connection piece 33.2. The adapter 33.1 consequently forms an intermediate adapter which can be connected, for example, between the adapters 1 and 1', if another medicament is required.

Figures 13, 14:
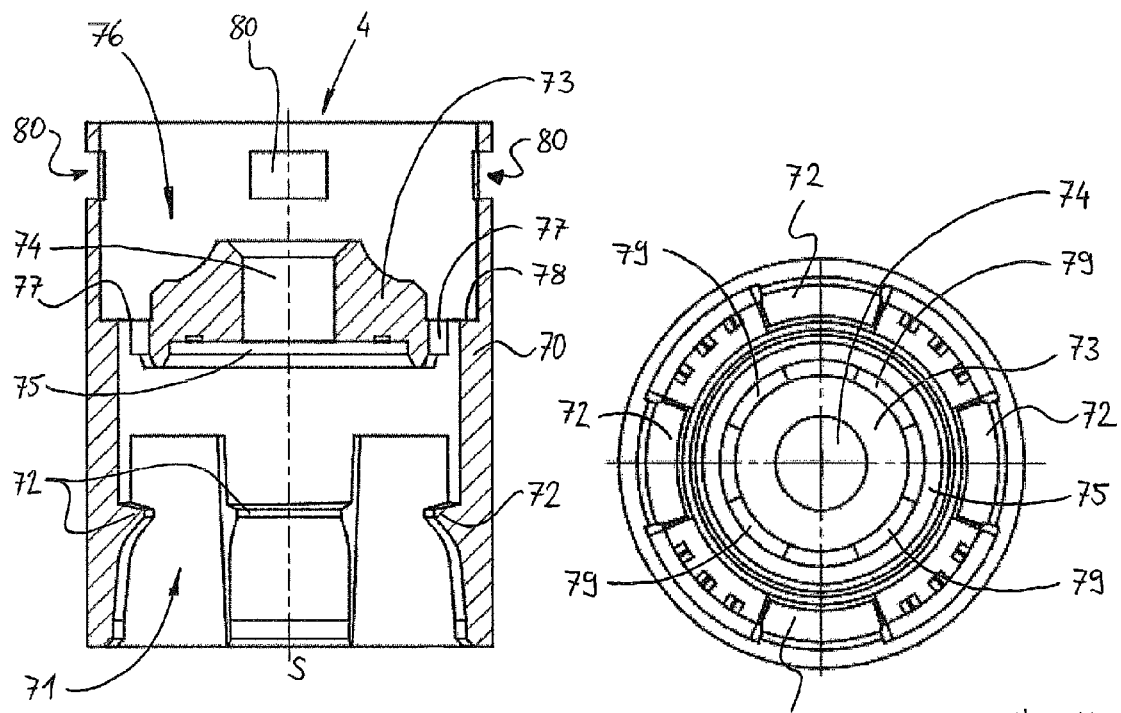
FIG. 13 is a longitudinal section of a cap member for an adapter.
FIG. 14 is a top view of the cap member of FIG. 13 in a longitudinal direction from a coupling side.

FIGS. 13 and 14 are a longitudinal section through a cap member 4 and a top view of a coupling side for coupling a container of a cap member 4, respectively.

The cap member 4 is preferably produced from a plastics material, in particular integrally as a molded component, for example, injection molded, and has a tubular base member 70. The cap member 4 has a coupling region 71 for coupling a container containing a liquid substance, for example, for the container 17. The cap member 4 can be positioned on a correspondingly formed container opening with the coupling region 71 in the manner of a sleeve. In the coupling region 71, there are formed on the inner walls of the base member 70 engaging projections 72 with which the cap member 4 can be snap-fitted on the container opening in the manner of a snap-fit collar. An outwardly projecting, peripheral annular bead 17.1 over which the engaging projections 72 in the snap-fitted state engage and thus engage the cap member 4 on the container is provided on the (standardized) container opening. The engaging projections 72 have such dimensions and are adapted to the (standardized) container opening so that the cap member 4 is securely retained on the container without any play and may optionally apply a sealing pressing force to a sealing element of the container.

A centering ring 73 which is arranged in a plane transverse relative to the longitudinal axis S of the cap member 4 and which has a central opening 74 is constructed in the tubular base member 70. The centering ring 73 delimits in the inner space of the base member 70 the coupling region 71 provided for coupling a container with respect to a receiving region 76 for a penetration element having guide means such as, for example, the penetration element 6 with a membrane 7 of the adapter 1. In the snap-fitted state of the cap member 4 on a container, the centering ring 73 adjoins a sealing element of the container and/or the container opening in a sealing manner at the coupling region side, wherein the sealing element can be clamped, for example, between an edge of the container opening and the centering ring 73.

The centering ring 73 has engaging recesses 77, in which snap-fit couplings of the guide means of a penetration element such as, for example, the snap-fit couplings 11 can be snap-fitted in order thus to secure the penetration element, for example, the penetration element 6, to the cap member. The guide means, that is to say, for example, the membrane 7, preferably have a support edge 7.1, which is supported on a corresponding peripheral projection 78 on the centering ring 73 in the snap-fitted state.

The central opening 74 is used to guide a hollow needle, for example, the hollow needle 9, of a penetration element, for example, the penetration element 6, if it is moved from the rest position R into the removal position E or is used for mechanical stabilization if the penetration element is in the removal position E.

At the coupling region side, the centering ring 73 has a receiving space 75 which is constructed annularly around the central opening 74 and in which a filter (not illustrated) is inserted in the ready-to-operate state. The receiving space 75 communicates via the ventilation opening 79 with the connection region 76 so that air from the atmosphere can be supplied to the receiving region 75 through the ventilation openings 79. In the snap-fitted state of the cap member 4 on a container, the centering ring 73 adjoins the sealing element and/or the container opening in such a sealing manner that, apart from the ventilation openings 79 and the central opening 74, the receiving space 75 is closed outwardly in a substantially air-tight manner.

If the penetration element 6 is in the receiving position E', the ventilation channel 2 which is in the form of a groove in the hollow needle 9 at the outer side adjoins the receiving space 75, wherein the central opening 74 of the hollow needle 9 arranged therein and/or the base member 8 of the penetration element 6 is sealed in a substantially air-tight manner. It is consequently possible to supply air from the atmosphere to the receiving space 75 and the ventilation channel 2 in the removal position E of the penetration element 6 only via the ventilation openings 79 and consequently via the filter arranged therein. As a result, it is ensured that air which reaches the connected container via the ventilation channel 2 must first pass the filter and is consequently free from germs and microorganisms and dirt.

In the connection region 76, there are further formed on the base member 70 engaging recesses 80, in which correspondingly formed engaging means of the penetration element, for example, the engaging means 19 of the penetration element 6, can engage when the penetration element 6 is in the removal position E.

It will be understood that the filter can be dispensed with in the case of corresponding cap members for adapters without a ventilation channel. In particular, the cap member 4' for an adapter 1' or 31 can be constructed in a substantially structurally identical manner without a filter being used.

Figures 15, 16:
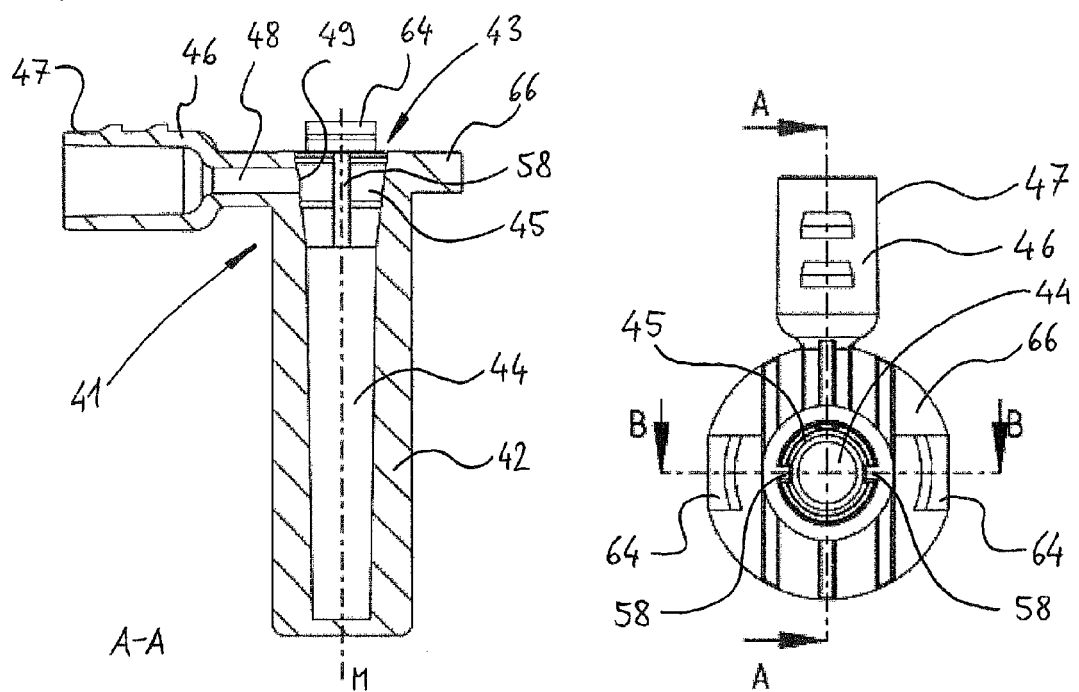
FIG. 15 is a longitudinal section of another embodiment of an adapter for coupling a discharge device to a sleeve for receiving an injection needle.
FIG. 16 is a top view of a coupling side of the adapter according to FIG. 15 in the longitudinal direction.
Figure 17:
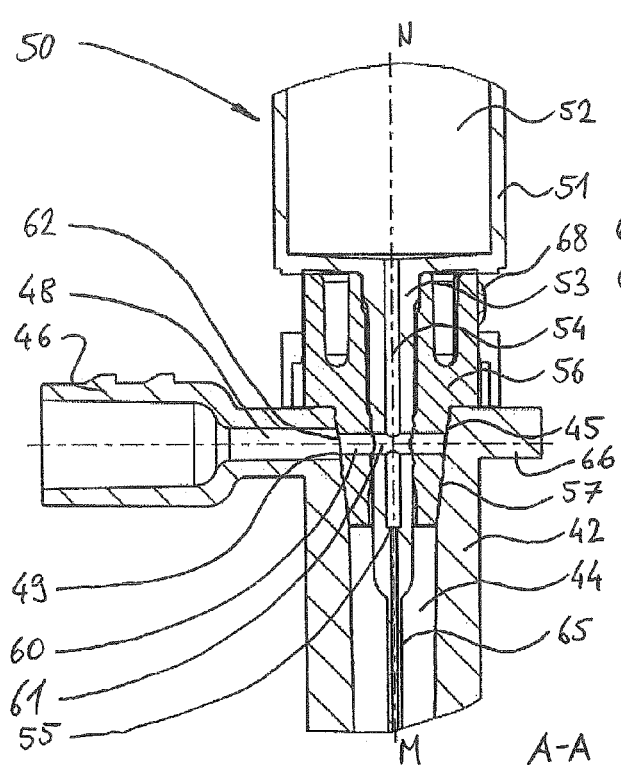
FIG. 17 is a cutout according to FIG. 15 with a discharge device coupled.
Figure 18:
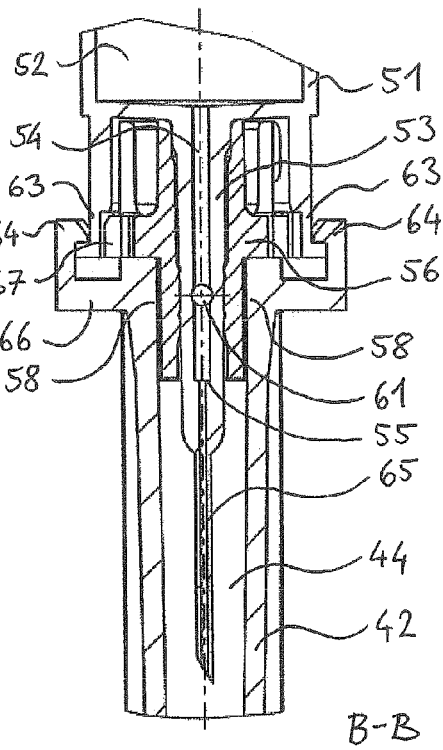
FIG. 18 is a cutout according to FIG. 17 in a plane of section which is perpendicular to the view of FIG. 17.

FIG. 15 is a cross section of another embodiment of an adapter 41 in the plane A according to FIG. 16, which adapter is provided only for supplying a fluid to a couplable discharge device (not illustrated; see FIGS. 17 and 18). FIG. 16 is a top view in the direction of the longitudinal axis M from a coupling side.

The adapter 41 comprises an elongate housing 42 which has a receiving space 44, which is open in the longitudinal direction M at an access opening 43, for a needle or cannula of the discharge device. A substantially conical seat 45 which is in the form of a coupling means is provided in a region at the opening 43. A connection piece 46, which has an end region 47 in the form of a connection coupling similarly to the end region 13' of the adapter 1', is constructed perpendicularly relative to the longitudinal direction M in a longitudinal region in the opening 43. The adapter 41 is consequently suitable for connection to the connection piece 3, for example, of the adapter 1, similarly to the adapter 1'. At the outer side, a retention plate 66 which projects outward in a plane perpendicular to M in the manner of a flange and in the plane of which the connection piece 46 is arranged is formed in the region of the connection piece 46.

A fluid channel 48 which is open at the connection piece 46 and which opens at an opening 49 on a lateral surface of the seat 45 is formed in the connection piece 46. Consequently, a fluid can be transferred via the fluid channel 48 from the connection piece 46 to the seat 45.

FIG. 17 is a cutout of the view according to FIG. 15, wherein a discharge device 50 is arranged in the adapter 41. The discharge device 50 is in a filling position in which it can be filled with a fluid via the adapter 41. FIG. 18 is a longitudinal section of the substantially identical cutout in a plane which is perpendicular relative to the plane of section of the views according to FIGS. 15 and 17 (plane B according to FIG. 16).

The discharge device 50 comprises an elongate base member 51 (longitudinal axis N) having an inner space 52 for receiving a fluid. At the front side, there is formed on the base member 51 a connection stud 53 which extends in the longitudinal direction N and which has an internal fluid channel 54. The fluid channel 54 connects the inner space 52 to a discharge opening 55 of the stud 53, to which discharge opening 55 an injection needle 65 is fitted. The injection needle 65 is arranged in the receiving space 44. The longitudinal direction M of the adapter 41 and the longitudinal direction N are substantially coaxially arranged in the coupled state.

Figure 19:
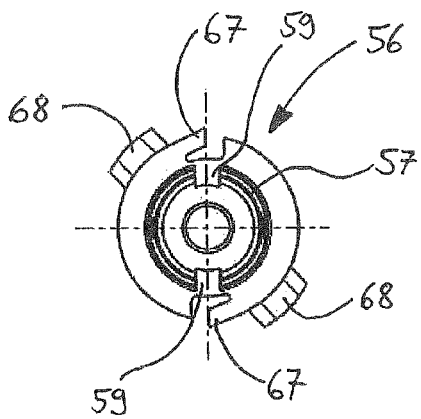
FIG. 19 is a top view of a cuff of the discharge device according to FIG. 17 in a longitudinal direction.
Figure 20:
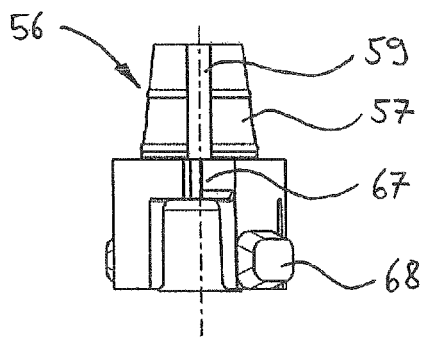
FIG. 20 is a lateral top view of the cuff according to FIG. 19.

An annular cuff 56 is supported on the connection stud 53 so as to be rotatable about the longitudinal axis N relative to the base member 51. The cuff 56 (illustrated alone in FIGS. 19 and 20) has a conical portion 57 which is constructed so as to substantially complement the seat 45 and with which it is arranged in the seat 45. Ribs 58 which are orientated in the longitudinal direction N, engage in corresponding grooves 59 of the cuff 56 and thus secure it against rotation are formed in the seat 45.

The cuff 56 has in the region of the opening 49 of the adapter 41 a transverse hole 60 which acts as a fluid channel and which is aligned with a corresponding transverse hole 61 in the connection stud 53 in the filling position and which opens at the outer side on the cuff 56 at a filling opening 62.

The filling opening 62 adjoins the fluid channel 48 of the adapter 41 in a fluid-tight manner in the filling position. The transverse hole 61 communicates with the fluid channel 54 and consequently produces a continuous fluid channel from the filling opening 62 to the inner space 52 of the discharge device in the filling position.

A coupling element 63 extends from the base member 51 in the longitudinal direction N (see FIGS. 18 and 21 to 23) at the outer side with spacing from the cuff 56. Coupling elements 64 which are complementary thereto and which are in engagement in a bayonet-like manner with the coupling element 63 in the filling position illustrated are constructed on the adapter 41.

If the discharge device 50 is full, the base member 51 is rotated about the longitudinal axis N in an uncoupling direction in relation to the adapter 41 in order to release the engagement of the coupling elements 63 and 64. The connection stud 53 is also rotated in this instance, wherein the rotationally secured cuff 56 remains at rest in relation to the adapter 41. The transverse holes 60 and 61 are therefore rotated relative to each other, whereby a fluid linkage is interrupted. The cuff 56 consequently acts as a tap system for sealing the filling opening 62 relative to the inner space 52. The engagement of the coupling elements 63 and 64 is also released in the event of adequate rotation of the base member 51 so that the discharge device 50 can be drawn out of the adapter 41 in the longitudinal direction N.

In order to ensure that the discharge device 50 is only suitable for one-time use and cannot be coupled again, the cuff 56 has engaging tongues 67 which cooperate with engaging notches 67.1 of the coupling element 63 in such a manner that rotation counter to the uncoupling direction is prevented in the manner of a safety catch. There are further formed at the peripheral side on the cuff 56 stops 68 which are arranged in recesses 68.1 of the coupling means 63 and which ensure that the base member 51 can be rotated only within a limited range in relation to the cuff 56, in particular in the uncoupling direction (see also in this regard FIGS. 21 to 23). The limited range predetermined by the recesses 68.1 is selected so that the discharge device 50, after a relative rotation which uses up the limited range in the uncoupling direction, the cuff 56 and base member 51 are secured in a position which prevents repeated coupling of the discharge device 50 to the adapter 41. It is therefore ensured that the discharge device 50 can be filled and used only once.

FIG. 21 is a view of the base member 51 of the discharge device 50 in the direction from N toward the discharge region without a cuff 56. FIGS. 22 and 23 are cutout views of longitudinal sections in the region of the discharge region of the discharge device 50 in the planes A and B according to FIG. 21, respectively, also without a cuff 56.

The coupling element 63 comprises a substantially circular-cylindrical pipe portion 63.1 which is arranged coaxially relative to the longitudinal direction N. The pipe portion 63.1 has substantially the same outer dimension as the base member 51 and extends in the discharge region in the longitudinal direction N away from the base member 51. The connection stud 53 is coaxially arranged in an inner space of the pipe portion 63.1. The cuff 56 is arranged partially in the inner space of the pipe portion 63.1 when the cuff 56 is positioned.

A finger flange 51.1 which is formed substantially in the manner of known syringes is provided at a longitudinal end of the base member 51 opposite the discharge region.

In an end region remote from the base member, the pipe portion 63.1 has at the outer side two wings 63.2 which project outward in the manner of flanges and which are arranged opposite in relation to the longitudinal direction N. The wings 63.2 form bayonet-like engaging means which are in engagement in the above-mentioned filling position with the correspondingly formed coupling elements 64 on the adapter 41.

The above-mentioned engaging notches 67.1 are also provided in the end region remote from the base member on the inner walls on the pipe portion 63.1 so as to extend in an azimuthal manner. The engaging notches 67.1 are formed and arranged in such a manner that, when the cuff 56 is inserted, the engaging tongues 67 thereof cooperate with the engaging notches 67.1 in the manner of a safety catch which prevents relative rotation of the base member 51 and the cuff 56 counter to the uncoupling direction.

The pipe portion 63.1 has two openings in the direction radial relative to N. The openings form the recesses 68.1 in which the stops 68 of the cuff 56 are arranged if the cuff is positioned on the base member 51. The recesses 68.1 extend over a predetermined azimuthal angular range which restricts the relative rotatability between the base member 51 and the cuff 56 to a limited range.

It will be understood that the coupling means of an adapter constructed substantially in accordance with adapter 1' may be constructed in such a manner that a discharge device in accordance with the discharge device 50 can be coupled and filled by means of the removal channel. To this end, a housing in accordance with the housing 42 can be constructed on such an adapter, for example, in a laterally offset manner, wherein the removal channel is guided to an opening on the lateral surface of the conical seat 45. The person skilled in the art will directly infer how such an embodiment can be implemented.

FIGS. 24 to 27 show different views of another embodiment of an adapter 100 of a device according to the invention without a cap member 104 (see in this regard FIGS. 29-31). FIGS. 24 to 27 are described together below.

The adapter 100 has a membrane 107 (substantially similar to the membrane 7, 7', 37) which is provided to connect the penetration element 106 (substantially similar to the penetration element 6, 6', 36) to a cap member 104 (see FIGS. 29-31). The membrane 107 is constructed in a dome-like manner and has a securing ring 107.1 in a region provided for securing to the cap member 104. The securing ring 107.1 is provided for securing the membrane 107 (and therefore the perforation element 106) to the cap member 104. The securing ring 107.1 is constructed in such a manner that it can be received in a connection region 176 of the cap member 104. For securing to the cap member 104, the securing ring 107.1 has two radially outwardly projecting engaging projections 111 which are arranged opposite each other in relation to the positioning direction W of the adapter 100. Those projections 111 can engage in a locking manner in corresponding engaging recesses 180 on the cap member 104 (see FIGS. 29-31). There are further arranged on the front side of the securing ring 107.1 four axial projections 111.1 which engage in corresponding recesses 177 of the cap member 104 (see FIGS. 29-31) in order to orientate the penetration element 106 axially.

The membrane 107 has four substantially circular flattened portions 116 which can be delimited, for example, by a predetermined breaking location. The membrane 107 may optionally burst at the transition into the removal position along those predetermined breaking lines. If bursting is desired in order, for example, to ensure an air supply where necessary, the membrane 107 may further have at the inner walls between the flattened portions 116 rigid perforation webs (not illustrated).

Figure 25:
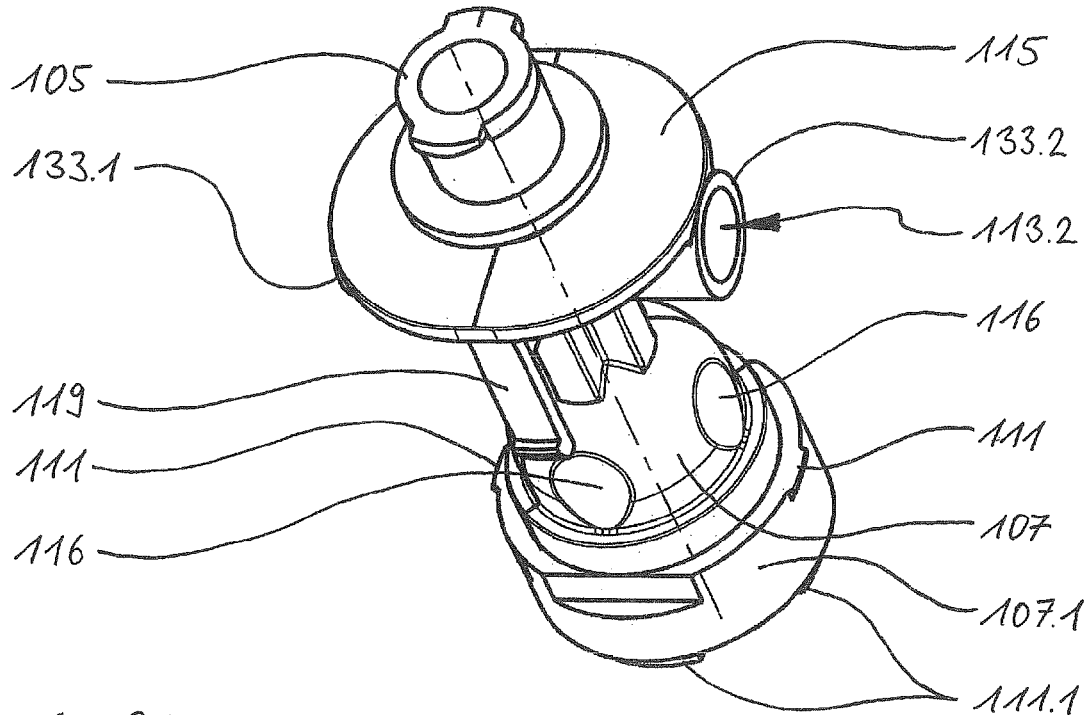
FIG. 25 is another external, oblique view of the adapter of FIG. 24.
Figure 26:
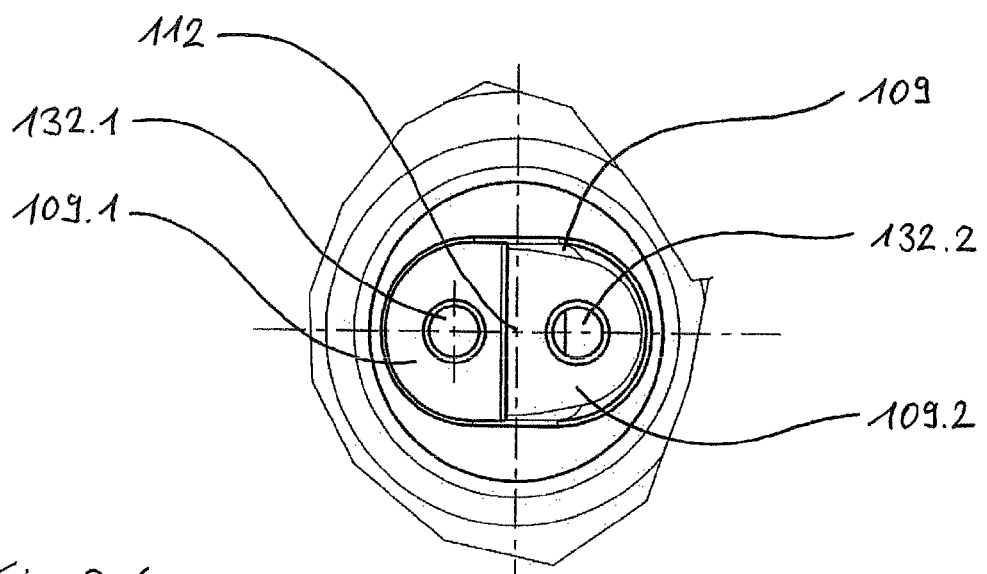
FIG. 26 is a detailed view of a hollow needle having two internal channels of the adapter according to FIG. 24.
Figure 27:
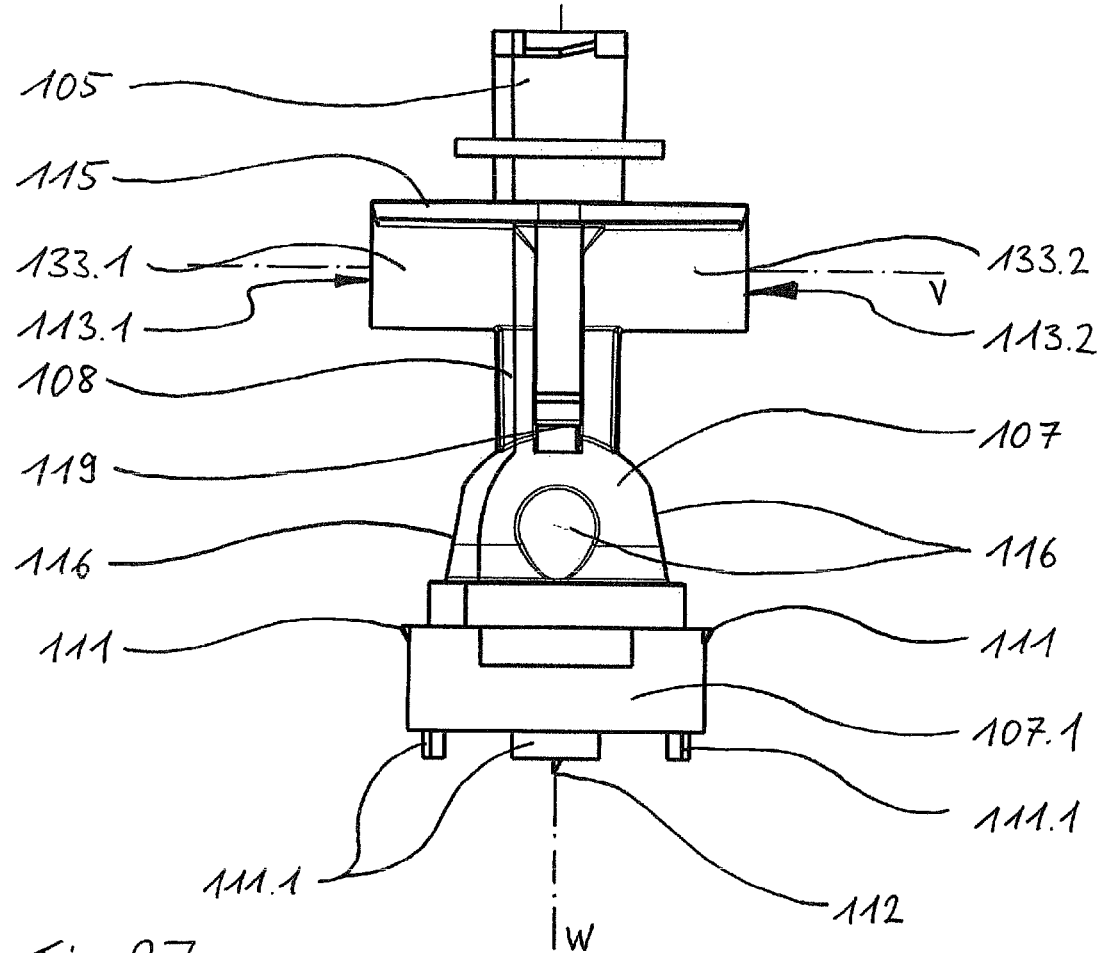
FIG. 27 is a side view from above of the adapter according to FIG. 24.

A substantially cylindrical base member 108 of the penetration element 106 adjoins the membrane 107 and continues outside the membrane 107 in a longitudinal direction. The base member 108 may have, for example, a circular or, as illustrated in FIGS. 24 and 25, a cross-like cross section. A first connection piece 133.1 and a second connection piece 133.2 are formed on the base member 108 with respect to the positioning direction W. The longitudinal axes of the two connection pieces 133.1 and 133.2 are located on a common axis V which is arranged perpendicularly to the positioning direction W of the adapter 100.

Each of the connection pieces 133.1 and 133.2 has a receiving space 113.1 and 113.2, respectively, for directly or indirectly coupling an additional adapter according to the invention. The receiving spaces 113.1 and 113.2 preferably have an inner cone as a coupling seat. In this manner, a corresponding outer cone of another adapter or a coupling piece 200 (see FIG. 33) can readily be connected in a fluid-tight manner to the connection pieces 133.1 and 133.2. Similarly, for example, a filter insert 190 may be inserted in the receiving spaces 113.1 and 113.2 if the corresponding connection piece is intended to act as a ventilation opening.

At the end side, the base member 108 merges into a connection coupling 105 of a Luer lock. A finger plate 115 projects transversely relative to the longitudinal direction of the penetration element 106 between the base member 108 and the Luer coupling 105 in a flange-like manner. A face of the finger plate 115 is constructed to be larger than a horizontal projection of the membrane 107 so that when viewed from above in a longitudinal direction the entire membrane 107 with the fixing ring 107.1 is covered by the finger plate 115.

The Luer coupling 105 is connected to a first fluid channel 132.1. The fluid channel 132.1 extends inside the base member 108 and a hollow needle 109 of the penetration element 106 (see FIGS. 28a-28b). The hollow needle 109 is arranged centrally inside the dome-like membrane 107 and extends in a longitudinal direction of the penetration element 106. The first fluid channel 132.1 opens in a region at a piercing tip 112 of the hollow needle 109 and is arranged eccentrically relative to a longitudinal axis of the hollow needle 109. In this manner, the central piercing tip 112 can be constructed in a solid manner for good penetration ability.

Two engaging tongues 119 which are arranged opposite each other with respect to the longitudinal direction of the penetration element 106 and which extend in the positioning direction W at both sides of the membrane 107 in the direction toward the securing ring 107.1 are formed on the finger plate 115. The engaging tongues 119 serve to engage the penetration element 106 on the cap member 104 in the removal position and to that end engage in the removal position in two additional recesses of the recesses 180 in the cap member 104 (see FIGS. 29 to 31).

The penetration element 106 is preferably produced together with the membrane 107 and the remaining elements illustrated in FIGS. 24 to 28c from plastics material as an integral molded component, in particular injection molded. Naturally, multiple-piece constructions are also conceivable.

FIG. 28a is a longitudinal section through the adapter 100 without a cap member 104. In the embodiment of FIG. 28a, an additional fluid channel 132.2 is formed in the hollow needle 109 and communicates in terms of fluid with the receiving space 113.2 of the connection piece 133.2. The second fluid channel 132.2 extends inside the hollow needle 109 in the longitudinal direction as far as a piercing tip 112 of the hollow needle 109. The second fluid channel 132.2 is also arranged eccentrically in the hollow needle 109 and also opens in a region on the piercing tip 112. The mouth openings of the two fluid channels 132.1 and 132.2 are arranged on oblique faces 109.1 and 109.2 of the piercing tip 112, which faces are arranged so as to be offset in the longitudinal direction of the hollow needle 109. In particular, the face 109.1 with the opening of the channel 132.1 is offset nearer the base member 108. In this manner, the mouth openings are arranged at different depths in a connected container in the removal position. In other words, the fluid channels 132.1 and 132.2 of the hollow needle 109 open in the container at different distances from the sealing element of the container.

As already described above in connection with other adapters according to the invention, another adapter according to the invention can be connected, directly or indirectly, to the connection piece 133.2 (for example, substantially similar to FIG. 10 or by means of a coupling member 200 according to FIG. 33). In the embodiment of FIG. 28a, the connection piece 133.1 is in the form of a blind connection piece and does not have any fluid connection with respect to one of the fluid channels 132.1 or 132.2. The adapter 100 according to FIG. 28a consequently corresponds substantially to the adapter 1' according to FIG. 6 with regard to the fluid guiding.

In an alternative application, the adapter 100 according to FIG. 28a can also be used alone, without additional connected adapters, in order to remove a liquid from a connected container. For removal, for example, a syringe is connected to the Luer coupling 105. By drawing on the syringe, there can be produced in the container a reduced pressure, with which the liquid can be drawn through the fluid channel 132.1. External air can flow inward into the container through the fluid channel 132.2. In order to ensure that the inwardly flowing air is not contaminated and/or is germ-free, the filter insert 190 may be inserted in the receiving space 113.2 of the connection piece 133.2 according to FIGS. 32a and 32b. The fluid channel 132.1 acts in this instance as a removal channel while the fluid channel 132.2 acts as a ventilation channel.

In that the mouth opening of the fluid channel 132.2 extends more deeply into the container than the mouth opening of the fluid channel 132.1, it is possible to prevent an air bubble from forming in the region of the mouth openings. Such air bubbles can produce an undesirable direct air seal between the two mouth openings as a result of the surface tension of the solvent or the solution in the container. Therefore, it is generally advantageous for the opening of a ventilation channel to be arranged in the longitudinal direction at a different height in the container from the height of the opening of a removal or transfer channel, wherein the opening of the ventilation channel is preferably arranged further away from the sealing element in the container than the opening of the removal channel or transfer channel.

FIG. 28b is a longitudinal section through the adapter 100 without a cap member 104. In FIG. 28b, the receiving space 113.1 of the connection piece 133.1 has a fluid connection 132.3 with respect to the fluid channel 132.1. As will be apparent from a comparison of FIGS. 28a and 28b, substantially the same adapter 100 can be used in order to provide two different fluid guides as a result of a slight modification, and consequently different possible uses of the adapter.

For example, the Luer coupling 105 of the adapter 100 can be sealed in accordance with FIG. 28b with a cap or a plug. In this manner, the adapter 100 has a substantially similar functionality to that of the adapter 31 described in FIG. 12. To this end, another adapter can be connected both to the connection piece 133.1 and to the connection piece 133.2. Alternatively, only one additional adapter may also be connected, for example, to the connection piece 133.1. The connection piece 133.2 may act as a ventilation opening for the incoming supply of air, wherein in this instance the filter insert 190 is preferably inserted into the receiving space 113.2. The fluid channel 132.2 acts as a ventilation channel in this instance. For example, a syringe may be connected via the Luer coupling 105 in order to introduce a solvent. After the solvent has been introduced, the solution can be transferred from the container via the connection piece 133.1 to the connected adapter. The empty syringe can seal the Luer coupling 105.

FIG. 28c shows another embodiment of an adapter 100' which has a substantially similar functionality to that of the adapter 31 described in FIG. 12. The fluid channels 132.1' and 132.2' of the adapter 100' communicate in terms of fluid directly with the receiving spaces 113.1' and 113.2'. The adapter 100' according to FIG. 28c does not have a Luer coupling.

The connection pieces 133.1 and 133.2 and the fluid channels 132.1 and 132.2 of the adapter 100 can be connected and used in different manners. This has significant technical advantages in terms of production because different adapters having only slight changes can readily be constructed in accordance with a single basic embodiment.

FIGS. 29 to 31 show a cap member 104 of the adapter 100 or 100', which cap member is provided for the penetration element 106 of FIGS. 24-28c, and are described together below.

The cap member 104 has a tubular base member 170 having a coupling region 171 for arranging an opening of a container, for example, the container 17/17'. A snap-fit collar having four inwardly projecting engaging projections 172 is formed in the coupling region 171 at the inner walls. A centering ring 173 which is arranged in a plane transverse to a longitudinal axis X of the cap member 104 and which has a central opening 174 is formed in the tubular base member 170. The centering ring 173 delimits the coupling region 171 provided for coupling the container in the inner space of the base member 170 with respect to the receiving region 176 for the penetration element 106.

The centering ring 173 has recesses 177 in which the projections 111.1 of the securing ring 107.1 engage in an axial direction in order to predetermine an axial orientation of the penetration element 106. Four engaging recesses 180 which are open outwardly in a radial direction are formed in the receiving region 176 at the outer side. The engaging projections 111 of the securing ring 107.1 can engage in two opposing engaging recesses 180, respectively, in order to secure the penetration element 106 with respect to withdrawal from the cap member 104. The two additional opposing engaging recesses 180 serve to engage the engaging tongues 119 of the penetration element 106 if it is located in the removal position. Unlike the cap members 4/4', no receiving space for a filter insert is provided in the case of the cap member 104. In this instance, a ventilation channel may be provided where necessary by one of the fluid channels 132.1 and 132.2 of the hollow needle 109, wherein filtering of the air is preferably achieved via the separate filter insert 190.

A substantial advantage of all the variants of cap members according to the invention such as, for example, 4, 4' or 104, is that they can be readily constructed for containers having a flange having a diameter of 13 mm or 20 mm or for containers having flanges of any diameter.

FIG. 32a is an external view of the filter insert 190. FIG. 32b is a longitudinal section through the filter insert 190. Both Figures are described together below.

The filter insert 190 has a base member 191 with a conical lateral surface 192. The base member 191 has a circular cross section. The conical lateral surface has such dimensions that the filter insert 190 can be inserted with frictional engagement in the conical seat of the receiving spaces 113.1 and 113.2 of the adapter 100 or 100'.

The base member 191 has an inner space 193 which is open at both longitudinal ends in order to allow a passage of air. For example, a filter member (not illustrated) such as, for example, a sintered filter, can be inserted in the inner space 193. In a preferable manner, however, a filter film (not illustrated) is sealed, such as, for example, adhesively bonded or (laser) welded, on the opening from the outer side at the tapered longitudinal end of the base member 191. In order to retain the filter and/or to protect it from mechanical effects, the filter insert 190 has at the tapered end a cross-like grid 194 in the opening arranged therein. In the region of the opposite opening, an inwardly projecting engaging bead 195 is formed in the inner space 193 and may retain a filter member in the inner space 193.

For all the embodiments according to the invention, in particular, for example, PET films or polycarbonate films through which extremely fine openings extend can advantageously be used as filters in addition to the conventional microfilter membranes or microfilter members. In place of separately inserted or bonded filters, they could also be integrated directly during injection molding of the respective carrier constructions or the filter insert.

FIG. 33 shows the coupling member 200 for indirectly connecting two adapters according to the invention. The coupling member 200 has a tubular base member 201 which is open at the end side and which has at the outer side a conical portion 202 or 203 in both end regions. The conical portions 202 and 203 are delimited with respect to each other by an externally extending, annular spacer 204. The conical portions 202 and 203 have such dimensions that the coupling member 200 can be inserted in a frictionally engaging manner in the conical seat of the receiving spaces 113.1 and 113.2 of the adapters 100 and 100', respectively. Retaining wings 205 which may be constructed for handling and for engagement of the coupling member 200, where applicable, with respect to the connection piece 133.1 and 133.2 are arranged on the spacer 204. The retaining wings 205 can further be constructed in such a manner that a relative orientation of two mutually connected adapters is provided in the event of cooperation with corresponding means on the connection pieces 133.1 and 133.2.

The invention claimed is:

1. An adapter for transferring fluid from a container which has a penetrable sealing element, said adapter comprising:
a cap member which can be positioned in a sealing manner in a positioning direction on a container opening which is sealed with the sealing element and on which a penetration element is supported in such a manner that the penetration element being displaceable by a guide between a rest position and a removal position, wherein the penetration element has a hollow needle which, in the removal position, penetrates the sealing element, and
a connection piece having a connection coupling for a fluid-tight connection of another adapter and a transfer channel extends from an opening in the connection piece as far as a first opening in the hollow needle so that, in the removal position of the penetration element, the transfer channel in the connection piece communicates with an inner space of the connected container the connection piece is arranged transversely relative to the positioning direction,
the adapter further comprises a coupling for connecting, in a coupling direction, with a discharge device and an additional fluid channel which is in the form of a removal channel extending from an opening in the coupling as far as a second opening in the hollow needle so that, when the penetration element is in the removal position, the opening of the removal channel in the coupling communicates with the inner space of a connected container.

2. The adapter as claimed in claim 1, wherein the guide has at least one wall portion which connects the penetration element to the cap member and retains the adaptor in the rest position, wherein the at least one wall portion can be deformed in such a manner that the at least one wall portion guides the penetration element until the removal position is reached.

3. The adapter as claimed in claim 2, wherein the at least one wall portion comprises at least one resilient membrane which surrounds the penetration element.

4. The adapter as claimed in claim 1, further comprising a ventilation channel for ventilating the container when the fluid is removed.

5. The adapter as claimed in claim 4, wherein the ventilation channel comprises a groove at an outer side of the hollow needle.

6. The adapter as claimed in claim 4, further comprising at least one filter via which air can be supplied in the removal position from atmosphere to the container via the ventilation channel.

7. The adapter as claimed in claim 6, wherein the filter is arranged on the cap member, in a retention member which surrounds the penetration element in the manner of a circular ring if the penetration element is in the removal position.

8. The adapter as claimed in claim 1, further comprising a second connection piece having a connection coupling for a fluid-tight connection with a second adapter and an additional fluid channel which is in the form of a second transfer channel extending from an opening in the second connection piece as far as the second opening in the hollow needle so that, when the penetration element is in the removal position, the opening of the second transfer channel in the second connection piece communicates with the inner space of a connected container, wherein the second connection piece is arranged transversely, relative to the positioning direction.

9. A transfer device for transferring a fluid from a container to a discharge device, comprising a first adapter as claimed in claim 4 and a second adapter which has a connection coupling.

10. The transfer device as claimed in claim 9, wherein the connection couplings of each of the first and the second adapters are constructed so as to complement each other in such a manner that the first adapter can be connected to the second adapter in a fluid-tight manner.

11. The transfer device as claimed in claim 9, wherein the connection couplings of the first and the second adapters are constructed in such a manner that the first and the second adapters can be coupled to each other in precisely two orientations, the connection direction of the first adapter and a coupling direction of the second adapter are opposed in a first of the two orientations and are aligned in a second of the two orientations, and the connection couplings predetermine the orientations of the first and the second adapters and secure the connection of the first and the second adapters produced by the two connection couplings.

12. The transfer device as claimed in claim 9, wherein a first of the connection couplings of the first and the second adapters comprises an outer cone and a second of the two connection couplings comprises an inner cone.

13. The transfer device as claimed in claim 9,
wherein the second adapter has a cap member which can be positioned in a sealing manner in a positioning direction on a second container opening which is sealed with a second sealing element and on which a penetration element of the second adapter is supported in such a manner that the penetration element of the second adapter is displaceable by a guide between a rest position and a removal position, wherein the penetration element of the second adapter has a hollow needle which, in the removal position, penetrates the second sealing element,
the second adapter has a first connection piece having the connection coupling for a fluid-tight connection with another adapter and a first transfer channel of the second adapter extends from an opening in the first connection piece of the second adapter as far as a first opening in the hollow needle of the second adapter so that the opening of the transfer channel in the connection piece of the second adapter communicates, in the removal position of the penetration element of the second adaptor, with an inner space of the connected second container; and
a second connection piece having a connection coupling for the fluid-tight connection of another adapter and an additional fluid channel which is in the form of a second transfer channel extending from an opening in the second connection piece of the second adapter as far as the first opening in the hollow needle of the second adapter so that, when the penetration element of the second adapter is in the removal position, the opening of the second transfer channel in the second connection piece communicates with the inner space of the connected second container,
the second connection piece is arranged transversely relative to the positioning direction, wherein the connection coupling of the first connection piece is constructed so as to complement the connection coupling of the first adapter and the connection coupling of the second connection piece is constructed so as to complement the connection coupling of the second adapter so that the additional adapter can be connected simultaneously to the first adapter and the second adapter directly in a fluid-tight manner.

14. The transfer device as claimed in claim 9, further comprising a common housing in which the first and the second adapters of the transfer device are arranged in a configuration provided for use.

15. A transfer device for transferring a fluid from first and second containers to a discharge device, said transfer device comprising first and second adapters, and the first adapter comprising:
a cap member which can be positioned in a sealing manner in a positioning direction on a first container opening which is sealed with a first sealing element and on which a penetration element of the first adapter is supported in such a manner that the penetration element of the first adapter being displaceable by a guide between a rest position and a removal position, and the penetration element of the first adapter has a hollow needle which, in the removal position, penetrates the first sealing element, and
a connection piece of the first adapter having a connection coupling for a fluid-tight connection with another adapter and a transfer channel of the first adapter extending from an opening in the connection piece as far as an opening in the hollow needle so that, in the removal position of the penetration element of the first adapter, the opening of the transfer channel in the connection piece of the first adapter communicates with an inner space of the connected first container,
wherein the connection piece of the first adapter is arranged transversely relative to the positioning direction, and the first adapter further comprises a ventilation channel for ventilating the first container when the fluid is removed,
the second adapter comprising a connection piece having a connection coupling for a fluid-tight connection with another adapter, and the connection piece of the second adapter having a transfer channel,
the connection coupling of the first and the second adapters are constructed in such a manner that the first and the second adapters can be coupled to each other in precisely two orientations, the connection direction of the first adapter and a coupling direction of the second adapter are opposed in a first of the two orientations and are aligned in a second of the two orientations, and the connection couplings predetermine the orientations of the first and the second adapters and secure the connection of the first and the second adapters produced by the two connection couplings.

16. A transfer device for transferring a fluid from first and second containers to a discharge device, said transfer device comprising first and second adapters, and the first adapter comprising:
a cap member which can be positioned in a sealing manner in a positioning direction on a first container opening which is sealed with a first sealing element and on which a penetration element of the first adapter is supported in such a manner that the penetration element of the first adapter being displaceable by a guide between a rest position and a removal position, and the penetration element of the first adapter has a hollow needle which, in the removal position, penetrates the first sealing element, and
a connection piece of the first adapter having a connection coupling for a fluid-tight connection with another adapter and a transfer channel of the first adapter extending from an opening in the connection piece as far as an opening in the hollow needle so that, in the removal position of the penetration element of the first adapter, the opening of the transfer channel in the connection piece of the first adapter communicates with an inner space of the connected first container,
wherein the connection piece of the first adapter is arranged transversely relative to the positioning direction, and the first adapter further comprises a ventilation channel for ventilating the first container when the fluid is removed,
the second adapter comprising:
a cap member which can be positioned in a sealing manner in a positioning direction on a second container opening which is sealed with a first sealing element and on which a penetration element of the second adapter is supported in such a manner that the penetration element of the second adapter being displaceable by a guide between a rest position and a removal position, and the penetration element of the second adapter has a hollow needle which, in the removal position, penetrates the second sealing element, and a connection piece of the second adapter having a connection coupling for a fluid-tight connection with another adapter and a transfer channel of the second adapter extending from an opening in the connection piece as far as an opening in the hollow needle so that, in the removal position of the penetration element of the second adapter, the opening of the transfer channel in the connection piece of the second adapter communicates with an inner space of the connected second container, wherein the connection piece of the second adapter is arranged transversely, relative to the positioning direction, the connection coupling of the connection piece of the first adapter is constructed so as to complement the connection coupling of the first adapter and the connection coupling of the connection piece of the second adapter is constructed so as to complement the connection coupling of the second adapter so that the additional adapter can be connected simultaneously to the first adapter and the second adapter directly in a fluid-tight manner.

\* \* \* \* \*